US012357740B2

United States Patent
Hornsby et al.

(10) Patent No.: US 12,357,740 B2
(45) Date of Patent: Jul. 15, 2025

(54) AUTOMATED PERITONEAL DIALYSIS SYSTEM HAVING A DRAIN PURGE

(71) Applicants: BAXTER INTERNATIONAL INC., Deerfield, IL (US); BAXTER HEALTHCARE SA, Glattpark (CH)

(72) Inventors: Jack Alexander Hornsby, Tempsford (GB); Lewis Siu Tai Ho, Hertfordshire (GB); Sergio Malorni, Cambridgeshire (GB); Jonathan Paul Cooke, Cambridge (GB); Akshaya Ahuja, St Neots (GB); Marco Troncone, Cambridge (GB)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 683 days.

(21) Appl. No.: 17/738,420

(22) Filed: May 6, 2022

(65) Prior Publication Data

US 2022/0355009 A1    Nov. 10, 2022

Related U.S. Application Data

(60) Provisional application No. 63/185,050, filed on May 6, 2021.

(51) Int. Cl.
*A61M 1/28* (2006.01)
*A61M 1/14* (2006.01)
*A61M 1/16* (2006.01)

(52) U.S. Cl.
CPC ............ *A61M 1/281* (2014.02); *A61M 1/154* (2022.05); *A61M 1/155* (2022.05);
(Continued)

(58) Field of Classification Search
CPC .... A61M 1/154; A61M 1/155; A61M 1/1565; A61M 1/159; A61M 1/1601;
(Continued)

(56) References Cited

U.S. PATENT DOCUMENTS

| 2007/0278155 A1 | 12/2007 | Lo et al. |
| 2012/0085707 A1 | 4/2012 | Beiriger |

(Continued)

FOREIGN PATENT DOCUMENTS

| EP | 2167160 B1 | 9/2015 |
| IT | BO20090649 A1 | 4/2011 |

OTHER PUBLICATIONS

International Preliminary Report on Patentability No. PCT/US2022/028067 dated Oct. 23, 2023.
(Continued)

*Primary Examiner* — John Kim
(74) *Attorney, Agent, or Firm* — K&L Gates LLP

(57) ABSTRACT

A peritoneal dialysis system comprises a cycler including a pump actuator; a disposable set including a pumping portion operable with the pump actuator, a patient line positioned to fluidly communicate with the pumping portion, and a drain container positioned to fluidly communicate with the pumping portion; and a control unit configured to cause the pump actuator to actuate the pumping portion to (i) run a peritoneal dialysis treatment in which fresh dialysis fluid is pumped through the patient line to a patient and used dialysis fluid is pumped from the patient to the drain container, and (ii) at the end of treatment, pump the used dialysis fluid from the drain container, through the patient line, to a house drain.

25 Claims, 9 Drawing Sheets

(52) U.S. Cl.
CPC .......... *A61M 1/1565* (2022.05); *A61M 1/159* (2022.05); *A61M 1/1601* (2014.02); *A61M 1/166* (2014.02); *A61M 1/282* (2014.02); *A61M 1/288* (2014.02); *A61M 2205/12* (2013.01); *A61M 2205/128* (2013.01); *A61M 2205/14* (2013.01); *A61M 2205/3331* (2013.01); *A61M 2205/3334* (2013.01); *A61M 2205/3344* (2013.01); *A61M 2205/3368* (2013.01); *A61M 2205/3386* (2013.01); *A61M 2205/3393* (2013.01); *A61M 2205/502* (2013.01)

(58) Field of Classification Search
CPC ...... A61M 1/166; A61M 1/281; A61M 1/282; A61M 1/288; A61M 2205/12; A61M 2205/128; A61M 2205/14; A61M 2205/3331; A61M 2205/3334; A61M 2205/3344; A61M 2205/3368; A61M 2205/3386; A61M 2205/3393; A61M 2205/502

See application file for complete search history.

(56) References Cited

U.S. PATENT DOCUMENTS

2014/0207055 A1 7/2014 Neftel et al.
2014/0276375 A1 9/2014 Minkus

OTHER PUBLICATIONS

Written Opinion PCT/US2022/028067 dated Oct. 23, 2023.
International Preliminary Report on Patentability for International Patent Application No. PCT/US2022/028059, mailed Nov. 16, 2023. 8 pages.
International Preliminary Report on Patentability No. PCT/US2022/028068 dated Mar. 23, 2023.
International Search Report for International Application No. PCT/US2022/028067 dated Dec. 2, 2022.

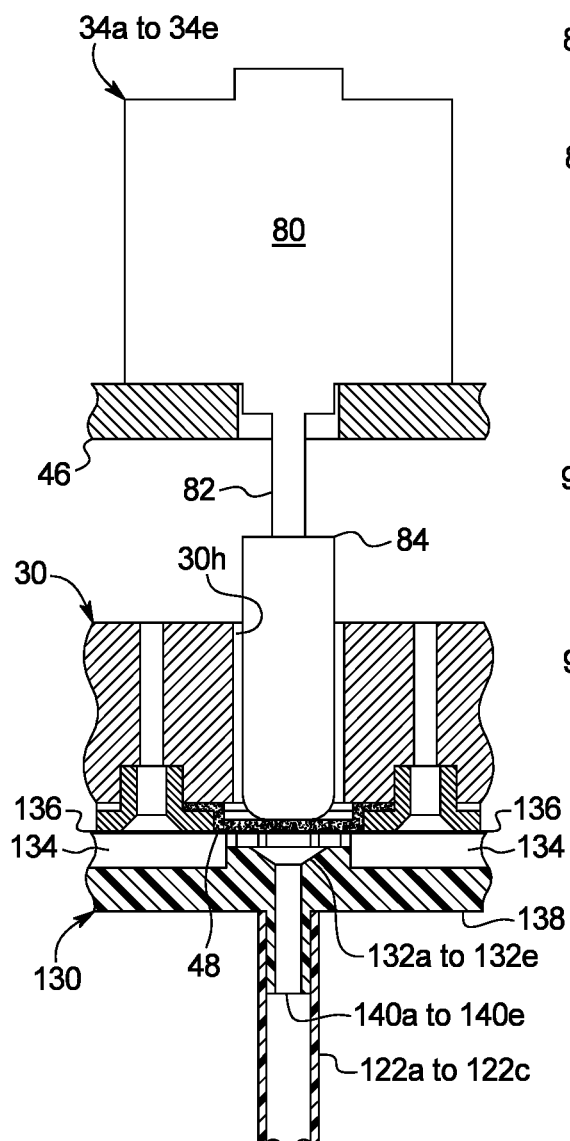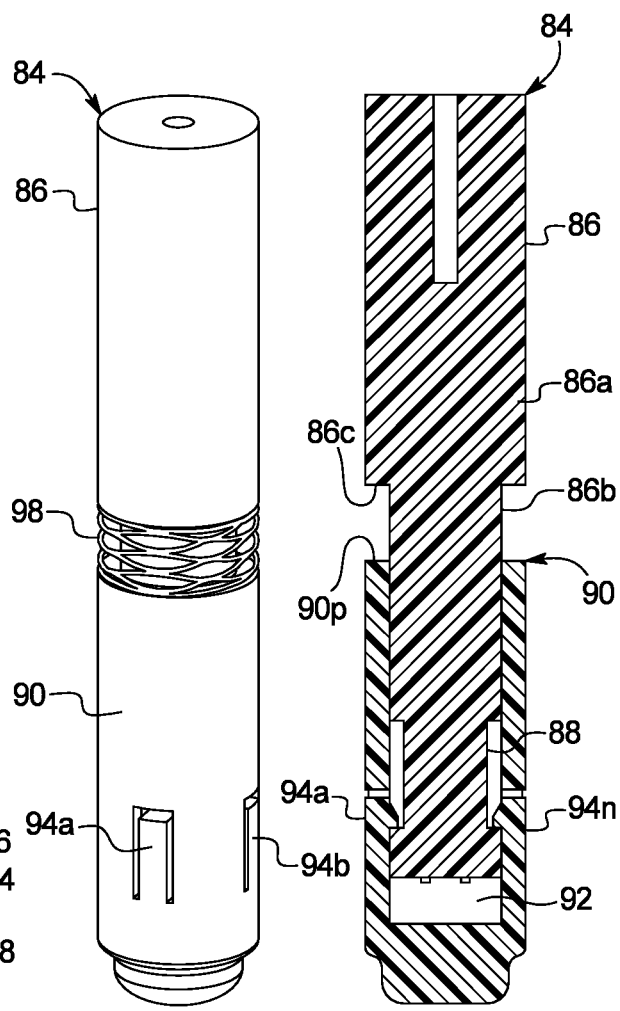
FIG. 4    FIG. 5A    FIG. 5B y = -0.0066x + 1.5591
y = -0.0084x + 1.5436
y = -0.0129x + 1.989
y = -0.009x + 1.8414

AUTOMATED PERITONEAL DIALYSIS SYSTEM HAVING A DRAIN PURGE

PRIORITY CLAIM

The present application claims priority to and the benefit of U.S. Provisional Application No. 63/185,050, entitled, Automated Peritoneal Dialysis Assembly, filed May 6, 2021, the entire contents of which are incorporated herein by reference and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Known APD systems include a machine or cycler that accepts and actuates a pumping cassette having a hard part and a soft part that is deformable for performing pumping and valving operations. Sealing the fluid disposable cassette with a pneumatic path via a gasket to provide actuation has proven to be a potential field issue, which can delay treatment start time and affect user experience. Pneumatic cassette systems also produce acoustic noise, which may be a source of customer dissatisfaction.

For each of the above reasons, an improved APD machine is needed.

SUMMARY

The present disclosure sets forth a streamlined automated peritoneal dialysis ("APD") system and associated cycler that uses a peristaltic pump and disposable set that organizes tubing and performs many functions discussed below. The cycler of the system in one embodiment includes a peristaltic pump actuator that is capable of pumping in two directions. Flow in either direction advances through a disposable cassette, which is part of an overall disposable set.

The disposable cassette is mounted within a housing of the cycler and is in one embodiment mounted vertically against an actuation surface of the housing and then enclosed between the actuation surface and a hinged door of the housing. A user interface communicating with a control unit is provided next to the door of the housing so that the patient or user generally interacts with one surface of the machine for inputting commands and receiving data and for loading the disposable cassette.

The system in one embodiment also includes a bag shelf enclosure that serves multiple purposes. The bag shelf enclosure is sized such that when the cycler is not in use, the cycler may be stored inside of the enclosure. The bag shelf enclosure is also sized such that when the cycler is in use, the bag shelf enclosure may be set on the top of the cycler. The bag shelf holds multiple containers or bags, such as multiple supply containers and one or more drain container. In one example, multiple supply containers are located within the bag shelf enclosure during treatment, while a drain container and a last fill container are located outside of and on top of the enclosure. The bag shelf enclosure may include color-coded markers provided at locations for loading containers or bags having lines that extend into the cycler through apertures, wherein the apertures have like color-coded markers. The matching color-coded markers make it easy for the patient or caregiver to identify which bag and line belongs at which location on the bag shelf enclosure.

It is contemplated to use the supply containers or bags later as drain containers or bags to reduce overall disposable cost. For example, assume that the patient is full of effluent at the beginning of treatment. That effluent is initially drained from the patient and delivered to an empty drain container. A first patient fill is then delivered from a first supply container to the patient, and after a specified dwell period, delivered to the same drain container or to a different drain container depending on the sizes of the drain container(s). The drain container(s) is/are used to receive effluent until the first supply container is emptied after which the first supply container receives effluent after a dwell period using PD fluid provided from a second supply container. The first supply container is used to receive effluent, perhaps over multiple patient fills, dwells and drains, until the second supply container is empty. At that point the patient may receive a last fill of a different formulation of peritoneal dialysis fluid, which remains within the patient until the next night treatment or perhaps until a midday exchange.

At the end of treatment, multiple containers or bags are full of effluent. To prevent the patient or caregiver from having to transport the drain bags to a house drain, e.g., toilet, sink or bathtub, the control unit of the cycler is programed to prompt the user to remove the patient line from the patient's transfer set and carry the distal end of the patient line to the house drain. It should be appreciated that "house drain" as used herein means any type of drain provided in any type of building or domicile, such as a home, apartment, work building, hospital, clinic, public or private facility, etc. If needed, a reusable extension line may be connected to the distal end of the patient line to reach the house drain. The patient or caregiver then presses a drain button on the user interface, upon which the cycler actuates the peristaltic pump actuator in a direction so as to pull used dialysis fluid or effluent from each of the drain containers (one or more of which may be former supply containers) and pump the used dialysis fluid through the patient line (and extension line if needed) to the house drain. The cycler detects when each drain container is empty (e.g., via a weigh scale and/or pressure sensor discussed in detail below) and automatically switches valve actuators, e.g., pinch valve actuators, to sequence between drain containers until each is emptied. The above sequence is repeated for any residual fresh dialysis fluid in a main supply or last fill container. It should be appreciated that multiple drain containers (one or more of which may be former supply containers) may be drained simultaneously or at the same time, e.g., to save time. In this manner, once the patient disconnects from the patient line and presses the drain button, the patient is free to begin their day.

As mentioned above, the cycler uses peristaltic pumping in one embodiment. A peristaltic pump actuator under control of the control unit is located on the actuation surface of the cycler. The disposable cassette includes a peristaltic pump tube that the user guides over the peristaltic pump actuator when loading the cassette. In operation, the peristaltic pump actuator compresses the peristaltic pump tube at multiple points against a raceway. The operational proximity of the raceway to the peristaltic pump actuator would make the loading of the tube difficult. The present cycler accordingly includes a moveable raceway that translates out of the way of the peristaltic pump actuator via a linkage when the patient or caregiver opens the door of the cycler to load the cassette. After the cassette is loaded, the closing of the cycler door causes the moveable raceway to translate via the linkage into operable position directly adjacent to the peristaltic pump tube. In an alternative embodiment, a motor and lead screw assembly, or a linear actuator (e.g., linear stepper motor) is provided to automatically translate the raceway out of the way of the peristaltic pump actuator when the patient or caregiver opens the door of the cycler to load the cassette and to automatically translate the raceway into the operable position when the door is closed. In a further alternative embodiment, motor and lead screw assembly, or a linear actuator (e.g., linear stepper motor) is provided, but the patient or caregiver instead presses one or more button on the user interface to translate the raceway out of the way or into the operable position.

In an embodiment, the raceway is mounted to a block or member that is translatable across the actuation surface towards and away from the peristaltic pump actuator. Besides the translatable motion of the member (and the raceway), the moveable raceway is also able to rotate about a pivot provided at one end of the raceway, wherein the pivot is mounted to the translatable member. The other end of the raceway is spring-loaded via a spring, e.g., compression spring, confined between the raceway end and the member. The spring pushes the raceway about the pivot into a desirable operating position around the peristaltic pumping tube when the member has been translated towards the peristaltic pump actuator. The pivoting raceway absorbs or allows for variances due to tubing tolerance and may also provide a dampening effect that aids noise reduction.

As mentioned above, the cycler uses pinch valve actuators in one embodiment, wherein the disposable cassette is provided with valve seats that receive the pinch valve actuators to occlude or close a fluid pathway provided by the disposable cassette. Here, the cassette is sealed to and covered by a flexible sheet, e.g., flexible plastic, that the pinch valve actuators press into respective valve seats to close a respective fluid pathway. The pinch valve actuators retract to open their respective fluid pathways.

The pinch valves are each driven by a linear actuator, which may be any suitable type of linear actuator, such as a linear stepper motor, which provides a necessary amount of travel (e.g., up to 10 mm) and a needed amount of pressurized cassette sheeting closing force (e.g., 30 to 60 Newtons ("N") or less). The linear actuator drives a valve plunger back and forth to press the cassette sheeting against, and allow the sheeting to be removed from, the cassette valve seat. The valve plunger in one embodiment includes a proximal end effector that couples to the linear actuator and a distal end effector that is slidingly coupled to the proximal end effector. A spring, such as a wave or compression spring, may be provided with the plunger and positioned so as to bias the distal end effector outwardly relative to the proximal end effector. The variable distance provided by the spring enables the pinch valve to contact the cassette sheeting initially at a lesser closing force, which increases steadily as the spring is compressed. In an embodiment, a flexible membrane, such as a silicone membrane, is fixed to the actuation surface so as to cover the end of distal end effector, such that the flexible membrane contacts the cassette sheeting. When the spring is fully compressed, the cassette sheeting sees the full force of the linear actuator and the spring. The spring accordingly provides a force buffer that helps to protect the flexible membrane over multiple treatments and the cassette sheeting over the course of a single treatment. The spring may also help with variances due to tolerance in the disposable cassette and the loading of the cassette, and may further allow for a smaller or less expensive linear actuator.

As mentioned, the disposable cassette provides multiple valves seats, which may include a patient line valve seat, first and second supply line valve seats, a last fill line valve seat and a drain line valve seat. In one embodiment, the patient line valve seat is separated fluidically from a first peristaltic tube port by an inline fluid heating pathway, e.g., a serpentine pathway. When the disposable cassette is mounted for operation, the inline fluid heating pathway is abutted against a heater, such as a resistive plate heater.

In one embodiment, the first and second supply line valve seats, a last fill line valve seat and a drain line valve seat are each located within a common well, which is in fluid communication with a second peristaltic tube port. In this manner, fresh dialysis fluid may be pumped from any of the supply containers for the first and second supply line valve seats or the last fill line valve seat in a first direction through the common well and the inline fluid heating pathway, where the fresh dialysis fluid is heated, and then pumped out the patient line valve seat to the patient. Used dialysis fluid or effluent may be pumped from the patient in a second direction through the patient line valve seat and the inline fluid heating pathway, where the used dialysis fluid is not heated, into the common well and out the drain line valve seat to a drain container.

Any of the valve seats described herein may include a tapered sealing surface surrounded by a plurality of displacement ribs, each extending from a rigid wall of the disposable cassette, wherein at least some of the displacement ribs are spaced apart to prevent or mitigate against an unwanted occlusion of the tapered sealing surface by the flexible sheet, and to allow fresh or used dialysis flow therethrough. The displacement ribs may be completely separate from each other or extend from a common cylindrical base. The displacement ribs may be separate from the tapered sealing surface or extend from an outer edge of the tapered sealing surface. The displacement ribs prevent ingress of the flexible sheet into the tapered sealing surface. The displacement ribs may also guide the respective pinch valve plunger towards a center of the valve seat, while also providing an amount of give or play between the pinch valve plunger and the valve seat. The tapered sealing surface in an embodiment tapers to form a funnel shape leading to an opening that allows fresh or used dialysis fluid to flow into or out of the valve seat. In an embodiment, the opening extends through a port located on the other side of a rigid body of the disposable cassette, wherein the port sealingly accepts (attaches to) a tube or line, such as a patient line, supply line or drain line. The tapered sealing surface may also include or define one or more circular sealing ring that presses into the flexible sheet when the flexible sheet is closed by the pinch valve.

In an embodiment, a first or patient pressure sensing pod is located in the disposable cassette directly adjacent to the patient line valve seat. The patient pressure sensing pod when the disposable cassette is loaded is abutted against a first or patient pressure sensor, which outputs to the cycler control unit. The patient pressure sensor output may be used to control positive and negative pumping pressures experienced by the patient to be within safe pressure limits. A second or pumping pressure sensing pod is located in the disposable cassette between the common well and the second peristaltic tube port. The pumping pressure sensing pod when the disposable cassette is loaded is abutted against a second or pumping pressure sensor, which outputs to the cycler control unit. The pumping pressure sensor output may be used to detect supply and drain line occlusions and/or supply empty conditions.

The disposable cassette may also include one or more area, which when loaded for operation abuts against a thermocouple or other temperature sensor outputting to the control unit. A temperature sensing area may for example be placed at the end of the inline fluid heating pathway directly adjacent to the patient pressure sensing pod, so that the outlet temperature of the fresh dialysis fluid to the patient may be monitored and controlled to a desired temperature, e.g., body temperature or 37° C. and e.g., via a proportional, integral, derivative ("PID") routine performed by the control unit using feedback from the temperature sensor. A second temperature sensor may located so as to detect a temperature at the inlet of the inline fluid heating pathway if needed, which may likewise provide useful information for the PID routine.

It is contemplated to mount the pressure sensors in the actuation surface of the cycler such that when the disposable cassette is loaded for operation, the cassette sheeting, which may be polyvinyl chloride ("PVC"), is contacted and placed under tension by the pressure sensor, creating a baseline force measured by the pressure sensor. Fresh or used dialysis fluid pressure displaces (or attempts to displace) the cassette sheeting further and thereby increases or decreases the fluid force acting on the pressure sensor relative to the baseline force. The force differences caused by positive or negative fluid pressure are correlated to actual fluid pressure values by the control unit, which are used for pressure control and which may be displayed by the user interface and/or stored for delivery to a remote computer for evaluation.

The pre-tensioning of the cassette sheeting by the pressure sensor results in a pressure sensing regime having high sensitivity and resolution, but which may be prone to temperature sensitivity. It is accordingly contemplated to compensate for temperature. Here, a voltage output (or current output) from the pressure sensor is modified by adding a component, which is a function of a measured temperature (e.g., using the thermocouple discussed above) multiplied by an empirically determined temperature scaling coefficient, to form a compensated voltage output, which is then converted or correlated to a compensated positive or negative pressure.

As mentioned above, the pre-tensioning of the cassette sheeting by the pressure sensor results in a pressure sensing regime having high sensitivity and resolution, but which may also be prone to mechanical creep sensitivity. To combat creep sensitivity, the control unit is programmed in one embodiment to precondition the cassette sheeting prior to treatment, e.g., during setup, so that much of the variance to the pressure signal due to creep is eliminated before the pressure measurements matter. To do so, the control unit after the disposable cassette is primed causes all pinch valves to close and then actuates the peristaltic pump actuator so as to pressurize the inside of the cassette, including the pressure pods, to stretch the cassette sheeting. The control unit may be programmed to cause the pump actuator to oscillate the cassette fluid pressure up and down cyclically multiple times over a specified duration, wherein the upper pressure may be, for example, from 100% to 150% of a maximum operational pressure set for treatment. The preconditioning of the cassette sheeting helps to make the uncompensated pressure reading more accurate, while the temperature compensation helps to make the final pressure reading more accurate.

The system and cycler of the present disclosure in one embodiment employ a weigh scale having multiple load cells to monitor the amount of fresh dialysis fluid delivered to the patient, the amount of used dialysis fluid removed from the patient, and from there enable the control unit to calculate an amount of ultrafiltration ("UF") removed from the patient. Weigh scales and load cells are advantageous for a number of reasons. First, weigh scales are relatively accurate compared with other volumetric measurement techniques. Second, the weigh scale reduces the pump cost because the pump actuator may be a relatively simple peristaltic pump actuator and the disposable portion of the pump may be a simple peristaltic pump tube.

One drawback of the use of load cells is calibration. Load cells may over time read inaccurately and therefore need to be recalibrated. The present cycler and associated system provide a weigh scale having multiple load cells and an onboard structure and methodology for calibrating the weigh scale. In one embodiment, the weigh scale includes a weigh plate located at the top of the cycler, which supports the weight of the bag shelf enclosure and each of the solution and drain containers and associated fresh and used dialysis fluid. The weigh plate and each of the weighted items on the weigh plate are supported by multiple, e.g., four, load cells that collectively measure the total mass placed on the weigh plate (bag shelf enclosure, containers and fluids). The onboard calibration structure in one embodiment includes a fifth load cell and a linear actuator (may be of the same type as used for the pinch valves) located between the fifth load cell and the weigh plate.

The linear actuator includes an actuation output shaft that is fixed to the weigh plate such that the linear actuator can apply a pulling or downward force to the weigh plate. In one implementation, the pulling force is applied to the center of mass of the underside of the weigh plate. The additional calibration load cell measures the total force applied, while the four operational load cells each measure a fraction or fourth of the total force. If the operational load cells are each performing properly, the sum of their outputs should equal the total force measured by the calibration load cell. In an example, suppose 1000 Newtons ("N") of pulling force is applied by the linear actuator. The calibration load cell should thereafter output 1000 N, while the equidistant operational load cells $102a$ to $102d$ should each read 250 N, totaling 1000 N in combination.

Because the calibration load cell is used infrequently, the calibration algorithm is applied assuming that the output of calibration load cell is more accurate than the collective outputs of the operational load cells, which are used throughout each treatment. So if during calibration there is a mismatch between what the calibration load cell reads versus the collective output of the operational load cells, the control unit using the calibration algorithm scales or offsets the collective output of the operational load cells to match that of the calibration load cell. In the above example, suppose the operational load cells actually collectively read 995 N instead of 1000 N. The operational load cells are accordingly reading low by 0.5%. The control unit is thereby configured during treatment to modify the collective output of the operational load cells by a calibration factor of 1000/995 or 1.005.

Because the calibration load cell is used infrequently, the calibration algorithm assumes that its output is more accurate than the collective output of the operational load cells, which are used throughout each treatment. So if during calibration there is a mismatch between what the calibration load cell reads versus the collective output of the operational load cells, the control unit using the calibration algorithm scales or offsets the collective output of the operational load cells to match that of the calibration load cell. In the above example, suppose the operational load cells actually collectively read 605 Newtons instead of 600 Newtons. The operational load cells therefore only sense 395 Newtons of the applied 400 Newtons. The operational load cells are accordingly reading low by 1.3%. The control unit of the cycler is thereby configured during treatment to modify the collective output of the operational sensors by a calibration factor of 400/395 or 1.01.

The load cell calibration routine or algorithm is performed on some desired basis, e.g., before the start of each treatment. It should also be appreciated that because many of the weight values monitored and collected during treatment are weight differences, error in the collective output of the operational load cells tends to cancel itself out, assuming that the error does not change over the course of treatment. For example, the mass associated with a patient fill volume of two liters is monitored and controlled by the collective output of the operational load cells recording a drop in mass over the course of the patient fill. The volume and mass associated with a patient drain may be preset in the control unit, e.g., be a factor, such as 1.3, multiplied by the fill volume to account for patient UF removed into the drain volume. The volume and mass associated with a patient drain may alternatively be left open-ended and be controlled instead by the sensing of a characteristic rise in negative pressure by the pumping pressure sensing pod and associated pressure sensor, indicating that the patient is essentially fully drained and that further draining may be uncomfortable for the patient. In either case, the operational load cells sense an increase in weight over the course of the patient drain, which should tend to cancel any error in the operational load cells.

In light of the disclosure set forth herein, and without limiting the disclosure in any way, in a first aspect, which may be combined with any other aspect or portion thereof, a peritoneal dialysis system comprises a cycler including a pump actuator; a disposable set including a pumping portion operable with the pump actuator, a patient line positioned to fluidly communicate with the pumping portion, and a drain container positioned to fluidly communicate with the pumping portion; and a control unit configured to cause the pump actuator to actuate the pumping portion (i) to run a peritoneal dialysis treatment in which fresh dialysis fluid is pumped through the patient line to a patient and used dialysis fluid is pumped from the patient to the drain container, and (ii) at the end of treatment, to pump the used dialysis fluid from the drain container, through the patient line, to a house drain.

In a second aspect of the present disclosure, which may be combined with any other aspect or portion thereof, the pump actuator is a peristaltic pump actuator and the pumping portion of the disposable set includes a peristaltic pump tube.

In a third aspect of the present disclosure, which may be combined with any other aspect or portion thereof, the peritoneal dialysis system includes an extension line configured to be connected to the patient line if needed to reach the house drain.

In a fourth aspect of the present disclosure, which may be combined with any other aspect or portion thereof, the extension line is reusable.

In a fifth aspect of the present disclosure, which may be combined with any other aspect or portion thereof, the peritoneal dialysis system includes a user interface communicating with the control unit, and wherein the user interface is configured to prompt a patient at the end of treatment to disconnect from the patient line and to move the patient line towards the house drain.

In a sixth aspect of the present disclosure, which may be combined with any other aspect or portion thereof, the peritoneal dialysis system includes a user interface communicating with the control unit, and wherein the user interface is configured to provide or enable a drain button at the end of treatment for initiating the pumping of the used dialysis fluid from the drain container, through the patient line, to the house drain.

In a seventh aspect of the present disclosure, which may be combined with any other aspect or portion thereof, the user interface is further configured to require a confirmation that the drain line is in fluid communication with the house drain prior to providing or enabling the drain button.

In an eighth aspect of the present disclosure, which may be combined with any other aspect or portion thereof, the cycler includes a patient valve actuator that operates with a patient valve seat provided by the disposable set, and a drain valve actuator that operates with a drain valve seat provided by the disposable set, and wherein the control unit is configured to cause the patient valve actuator and the drain valve actuator to allow flow through the patient valve seat and the drain valve seat to pump the used dialysis fluid from the drain container, through the patient line, to the house drain.

In a ninth aspect of the present disclosure, which may be combined with any other aspect or portion thereof, at least one of the patient valve actuator or the drain valve actuator is a pinch valve actuator.

In a tenth aspect of the present disclosure, which may be combined with any other aspect or portion thereof, the peritoneal dialysis system includes a supply container positioned to fluidly communicate with the pumping portion of the disposable set, wherein the supply container is used during the peritoneal dialysis treatment for pumping fresh dialysis fluid through the patient line to the patient.

In an eleventh aspect of the present disclosure, which may be combined with any other aspect or portion thereof, the supply container is used later during the peritoneal dialysis treatment for receiving used dialysis fluid from the patient.

In a twelfth aspect of the present disclosure, which may be combined with any other aspect or portion thereof, the cycler includes a sensor in operable communication with the control unit, and wherein the control unit is configured to use an output from the sensor to determine when one of the drain container or the supply container used later as a drain container is empty or substantially empty after pumping its used dialysis to the house drain, and to thereafter switch to the other of the drain container or the supply container used later as a drain container to pump its used dialysis to the house drain.

In a thirteenth aspect of the present disclosure, which may be combined with any other aspect or portion thereof, the sensor is a weight sensor or a pressure sensor.

In a fourteenth aspect of the present disclosure, which may be combined with any other aspect or portion thereof, the control unit is further configured to cause the pump actuator to actuate the pumping portion at the end of treatment to pump remaining fresh dialysis fluid from the supply container, through the patient line, to the house drain.

In a fifteenth aspect of the present disclosure, which may be combined with any other aspect or portion thereof, the drain container is a first drain container and which includes a second drain container positioned to fluidly communicate with the pumping portion of the disposable set, wherein the cycler includes a sensor in operable communication with the control unit, and wherein the control unit is configured to use an output from the sensor to determine when the first drain container is empty or substantially empty after pumping its used dialysis to the house drain, and to thereafter switch to the second drain container to pump its used dialysis to the house drain.

In a sixteenth aspect of the present disclosure, which may be combined with any other aspect or portion thereof, the sensor for the fifteenth aspect is a weight sensor or a pressure sensor.

In a seventeenth aspect of the present disclosure, which may be combined with any other aspect or portion thereof, the drain container is a first drain container, and which includes a second drain container positioned to fluidly communicate with the pumping portion of the disposable set, and wherein the control unit is configured to drain the first and second drain containers at the same time.

In an eighteenth aspect of the present disclosure, which may be combined with any other aspect or portion thereof, a peritoneal dialysis system comprises a cycler including a pump actuator; a disposable set including a pumping portion operable with the pump actuator, a patient line positioned to fluidly communicate with the pumping portion, and a drain line positioned to fluidly communicate with the pumping portion; and a control unit configured to cause the pump actuator to actuate the pumping portion (i) to run a peritoneal dialysis treatment in which fresh dialysis fluid is pumped through the patient line to a patient and used dialysis fluid is pumped from the patient though the drain line, and (ii) at the end of treatment, to pump the used dialysis fluid through the drain line and the patient line, to a house drain.

In a nineteenth aspect of the present disclosure, which may be combined with any other aspect or portion thereof, the drain line is in fluid communication with a drain container, and wherein the drain container is provided initially as a drain container or a supply container filled with fresh dialysis fluid.

In a twentieth aspect of the present disclosure, which may be combined with any other aspect or portion thereof, the patient line and the drain line are separated by a disposable cassette of the disposable set, and wherein at the end of treatment, the used dialysis fluid is pumped through the drain line, through the disposable cassette, and through the patient line, to the house drain.

In a twenty-first aspect of the present disclosure, which may be combined with any other aspect or portion thereof, the disposable cassette includes a pressure sensing pod positioned to enable a pressure change indicative of a drain container in fluid communication with the drain line being empty to be detected, and wherein the control unit thereafter causes a switch to draining used dialysis fluid from a different source at the end of treatment to the house drain.

In a twenty-second aspect of the present disclosure, which may be combined with any other aspect or portion thereof, the cycler includes a weigh scale, wherein a drain container in fluid communication with the drain line is located so as to be weighed by the weigh scale, and wherein an output from the weigh scale indicative of the drain container being empty is used by the control unit to cause a switch to draining used dialysis fluid from a different source at the end of treatment to the house drain.

In a twenty-third aspect of the present disclosure, which may be combined with any other aspect or portion thereof, a peritoneal dialysis system comprises a cycler including a pump actuator; a disposable set including a pumping portion operable with the pump actuator, a patient line positioned to fluidly communicate with the pumping portion, and a drain container positioned to fluidly communicate with the pumping portion; and a control unit configured to cause the pump actuator to actuate the pumping portion (i) to run a peritoneal dialysis treatment in which fresh dialysis fluid is pumped through the patient line to a patient and used dialysis fluid is pumped from the patient to the drain container, and (ii) at the end of treatment, to pump the used dialysis fluid from the drain container, through the patient line, to a desired destination.

In a twenty-fourth aspect of the present disclosure, which may be combined with any other aspect or portion thereof, the desired destination includes a house drain or another container positioned to fluidly communicate with the pumping portion.

In a twenty-fifth aspect of the present disclosure, which may be combined with any other aspect or portion thereof, pumping the used dialysis fluid from the drain container through the patient line during (ii) includes actuating the pumping portion in a first direction to at least partially fill the patient line with the used dialysis fluid and then actuating the pumping portion in a second direction to remove the used dialysis from the patient line to the desired destination.

In a twenty-sixth aspect of the present disclosure, which may be combined with any other aspect or portion thereof, a disposable medical fluid cassette includes a pumping portion; a patient line valve seat positioned to fluidly communicate with the pumping portion; a rigid body defining a common well, the common well in fluid communication with the pumping portion; at least one supply line valve seat located in the common well; and a drain line valve seat located in the common well.

In a twenty-seventh aspect of the present disclosure, which may be combined with any other aspect or portion thereof, the patient line valve seat is provided by the rigid body.

In a twenty-eighth aspect of the present disclosure, which may be combined with any other aspect or portion thereof, the pumping portion includes a peristaltic pump tube attached to the rigid body.

In a twenty-ninth aspect of the present disclosure, which may be combined with any other aspect or portion thereof, the pumping portion includes a pump chamber defined by the rigid body.

In a thirtieth aspect of the present disclosure, which may be combined with any other aspect or portion thereof, the rigid body defines an inline fluid heating pathway located between the patient line valve seat and the pumping portion.

In a thirty-first aspect of the present disclosure, which may be combined with any other aspect or portion thereof, the disposable medical fluid cassette includes a temperature sensing area located between the patient line valve seat and the inline fluid heating pathway.

In a thirty-second aspect of the present disclosure, which may be combined with any other aspect or portion thereof, the inline fluid heating pathway is configured such that fresh dialysis fluid flows upwardly during priming to remove air through the patient line valve seat.

In a thirty-third aspect of the present disclosure, which may be combined with any other aspect or portion thereof, the disposable medical fluid cassette includes at least one of a pumping pressure sensing pod located between the drain line valve seat and a first end of the inline fluid heating pathway or a patient pressure sensing pod located between the patient line valve seat and a second end of the inline fluid heating pathway.

In a thirty-fourth aspect of the present disclosure, which may be combined with any other aspect or portion thereof, the disposable medical fluid cassette includes at least one of a patient line in fluid communication with the patient line valve seat, at least one supply line in fluid communication with the at least one supply line valve seat, or a drain line in fluid communication with the drain line valve seat.

In a thirty-fifth aspect of the present disclosure, which may be combined with any other aspect or portion thereof, the disposable medical fluid cassette includes at least one of a pumping pressure sensing pod located adjacent to the patient line valve seat or a pumping pressure sensing pod located adjacent to the common well.

In a thirty-sixth aspect of the present disclosure, which may be combined with any other aspect or portion thereof, the disposable medical fluid cassette includes a flexible sheet sealed to the rigid body, the flexible sheet flexed to open and close the at least one supply line valve seat and the drain line valve seat.

In a thirty-seventh aspect of the present disclosure, which may be combined with any other aspect or portion thereof, the rigid body includes rigid walls defining the common well, the flexible sheet sealed to the rigid walls to enclose the common well.

In a thirty-eighth aspect of the present disclosure, which may be combined with any other aspect or portion thereof, at least one of the patient line valve seat, the at least one supply line valve seat or the drain line valve seat includes a tapered sealing surface surrounded by a plurality of displacement ribs, at least some of the displacement ribs spaced apart to mitigate against flexible sheet ingress into the tapered sealing surface.

In a thirty-ninth aspect of the present disclosure, which may be combined with any other aspect or portion thereof, the common well includes a ramp configured to direct air in the common well towards the drain line valve seat.

In a fortieth aspect of the present disclosure, which may be combined with any other aspect or portion thereof, the drain line valve seat is positioned relative to the at least one supply line valve seat in the common well, such that the drain line valve seat is elevationally higher than the at least one supply line valve seat to direct air towards the drain line valve seat when the disposable medical fluid cassette is loaded for operation.

In a forty-first aspect of the present disclosure, which may be combined with any other aspect or portion thereof, a peritoneal dialysis system comprises a cycler including a pump actuator, a patient line valve actuator, at least one supply line valve actuator, and a drain line valve actuator; and a disposable medical fluid cassette including a pumping portion configured to operate with the pump actuator, a patient line valve seat configured to operate with the patient line valve actuator, a rigid body defining a common well, at least one supply line valve seat located in the common well and configured to operate with at least one supply line valve actuator, and a drain line valve seat located in the common well and configured to operate with the drain line valve actuator.

In a forty-second aspect of the present disclosure, which may be combined with any other aspect or portion thereof, the cycler is configured to perform a patient drain in which used dialysis fluid enters the common well followed by a patient fill in which fresh dialysis fluid enters the common well.

In a forty-third aspect of the present disclosure, which may be combined with any other aspect or portion thereof, during the patient drain, the drain line valve actuator is actuated so that used dialysis fluid is able to exit the common well via the drain line valve seat, and wherein during the patient fill, one of the at least one supply line valve actuators is actuated so that fresh dialysis fluid is able to enter the common well via one of the at least one supply line valve seats.

In a forty-fourth aspect of the present disclosure, which may be combined with any other aspect or portion thereof, during the patient drain and the patient fill, the patient line valve actuator is actuated so that used and fresh dialysis fluid, respectively, is able to flow through the patient line valve seat.

In a forty-fifth aspect of the present disclosure, which may be combined with any other aspect or portion thereof, a valve seat for a disposable medical fluid cassette includes a rigid wall; a tapered sealing surface extending from the rigid wall, the tapered sealing surface surrounding an opening formed in the rigid wall; and a plurality of displacement ribs extending from the rigid wall, or from an outer edge of the tapered sealing surface, so as to surround the tapered sealing surface, the displacement ribs spaced apart to mitigate against unwanted occlusion of the tapered sealing surface.

In a forty-sixth aspect of the present disclosure, which may be combined with any other aspect or portion thereof, the displacement ribs are separate from each other or extend from a common cylindrical base.

In a forty-seventh aspect of the present disclosure, which may be combined with any other aspect or portion thereof, the tapered sealing surface is cylindrical and the displacement ribs collectively form a cylindrical shape surrounding the tapered sealing surface.

In a forty-eighth aspect of the present disclosure, which may be combined with any other aspect or portion thereof, the tapered sealing surface forms a funnel shape that leads to the opening.

In a forty-ninth aspect of the present disclosure, which may be combined with any other aspect or portion thereof, the opening extends through a port located on an opposing side of the rigid wall from the tapered sealing surface and the displacement ribs.

In a fiftieth aspect of the present disclosure, which may be combined with any other aspect or portion thereof, the tapered sealing surface includes at least one circular sealing ring for pressing into a mating sealing member.

In a fifty-first aspect of the present disclosure, which may be combined with any other aspect or portion thereof, a pinch valve includes a linear actuator; a proximal end effector coupled to the linear actuator; a distal end effector slidingly engaged to the proximal end effector; and a spring positioned and arranged to bias the distal end effector outwardly relative to the proximal end effector.

In a fifty-second aspect of the present disclosure, which may be combined with any other aspect or portion thereof, the linear actuator incudes a linear stepper motor.

In a fifty-third aspect of the present disclosure, which may be combined with any other aspect or portion thereof, the proximal end effector and the distal end effector form a valve plunger.

In a fifty-fourth aspect of the present disclosure, which may be combined with any other aspect or portion thereof, the proximal end effector includes a larger diameter portion and a smaller diameter portion, and wherein the distal end effector includes a cylindrical opening that slidingly receives the smaller diameter portion of the proximal end effector.

In a fifty-fifth aspect of the present disclosure, which may be combined with any other aspect or portion thereof, the spring is positioned between a step transitioning between the larger and smaller diameter portions and the distal end effector.

In a fifty-sixth aspect of the present disclosure, which may be combined with any other aspect or portion thereof, the spring is constrained by the smaller diameter portion of the proximal end effector.

In a fifty-seventh aspect of the present disclosure, which may be combined with any other aspect or portion thereof, an outer diameter of the distal end effector is at least substantially equal to that of the larger diameter portion of the proximal end effector.

In a fifty-eighth aspect of the present disclosure, which may be combined with any other aspect or portion thereof, the spring is a wave spring or a compression spring.

In a fifty-ninth aspect of the present disclosure, which may be combined with any other aspect or portion thereof, one of the proximal end effector or the distal end effector defines at least one groove and the other of the proximal end effector or the distal end effector includes at least one spring arm that mechanically fits into the at least one groove.

In a sixtieth aspect of the present disclosure, which may be combined with any other aspect or portion thereof, the at least one groove is sized to provide a length of travel of the distal end effector relative to the proximal end effector, which is equal to or greater than an uncompressed length of the spring.

In a sixty-first aspect of the present disclosure, which may be combined with any other aspect or portion thereof, a dialysis machine includes an actuation surface against which a fluid carrying member is loaded to perform a dialysis treatment; a hole formed in the actuation surface; and a pinch valve including a linear actuator, a proximal end effector coupled to the linear actuator, a distal end effector slidingly engaged to the proximal end effector, and a spring positioned and arranged to bias the distal end effector outwardly relative to the proximal end effector, wherein the pinch valve is mounted within the machine such that the distal end effector extends through the hole to occlude a portion of the fluid carrying member.

In a sixty-second aspect of the present disclosure, which may be combined with any other aspect or portion thereof, the hole is covered by a flexible membrane, and wherein the distal end effector flexes the flexible membrane to occlude a portion of the fluid carrying member.

In a sixty-third aspect of the present disclosure, which may be combined with any other aspect or portion thereof, the pinch valve is mounted within the machine such that the spring is compressed prior to the portion of the fluid carrying member seeing a full occlusion force applied by the linear actuator.

In a sixty-fourth aspect of the present disclosure, which may be combined with any other aspect or portion thereof, the hole is a first hole and the pinch valve is a first pinch valve, wherein the actuation surface defines a second hole adjacent to the first hole, and which includes a second pinch valve mounted within the machine, such that a distal end effector of the second pinch valve extends through the second hole to occlude a second portion of the fluid carrying member.

In a sixty-fifth aspect of the present disclosure, which may be combined with any other aspect or portion thereof, the dialysis machine includes a control unit programmed to sequence the first and second pinch valves according to a preprogrammed sequence.

In a sixty-sixth aspect of the present disclosure, which may be combined with any other aspect or portion thereof, a dialysis machine operable with a disposable set having a peristaltic pumping tube includes an actuation surface for receiving the disposable set; a peristaltic pump actuator extending from the actuation surface, the peristaltic pump actuator operable with the peristaltic pumping tube; a member translatable along the actuation surface; a raceway pivotally connected at a first end to the member via a pivot; and a spring biased to push a second end of the raceway about the pivot and outwardly from the member.

In a sixty-seventh aspect of the present disclosure, which may be combined with any other aspect or portion thereof, the dialysis machine includes a stop positioned to limit a distance that the spring is able to push the second end of the raceway outwardly from the member.

In a sixty-eighth aspect of the present disclosure, which may be combined with any other aspect or portion thereof, the spring is disposed about the stop.

In a sixty-ninth aspect of the present disclosure, which may be combined with any other aspect or portion thereof, the stop is connected to and travels with the member.

In a seventieth aspect of the present disclosure, which may be combined with any other aspect or portion thereof, the stop extends through an aperture or opening formed in the second end of the member and includes a head larger than at least one dimension of the aperture or opening, the spring biased to push the second end of the member against the head.

In a seventy-first aspect of the present disclosure, which may be combined with any other aspect or portion thereof, the spring is a compression or tension spring.

In a seventy-second aspect of the present disclosure, which may be combined with any other aspect or portion thereof, the member includes a base defining an arc having a radius that at least substantially matches a radius of the raceway.

In a seventy-third aspect of the present disclosure, which may be combined with any other aspect or portion thereof, the dialysis machine includes a stop positioned to stop a pivoting of the raceway caused by the spring when the radius of the raceway at least substantially reaches the radius of the arc.

In a seventy-fourth aspect of the present disclosure, which may be combined with any other aspect or portion thereof, the actuation surface defines a linear rail along which the member translates, an underside surface of the member including a rail receiver sized to operate with the linear rail.

In a seventy-fifth aspect of the present disclosure, which may be combined with any other aspect or portion thereof, the linear rail and rail receiver are formed such that the linear rail holds the member slidingly against the actuation surface.

In a seventy-sixth aspect of the present disclosure, which may be combined with any other aspect or portion thereof, the member defines at least one slot for enabling the member to be slidingly attached to the actuation surface.

In a seventy-seventh aspect of the present disclosure, which may be combined with any other aspect or portion thereof, the dialysis machine includes a door configured to be opened and closed relative to the actuation surface, and which further includes a linkage positioned and arranged to translate the raceway away from the peristaltic pump actuator when the door is opened and to translate the raceway into an operable position relative to the peristaltic pump actuator when the door is closed.

In a seventy-eighth aspect of the present disclosure, which may be combined with any other aspect or portion thereof, the dialysis machine includes a door configured to be opened and closed relative to the actuation surface, and which further includes a motorized assembly configured to translate the raceway away from the peristaltic pump actuator and to translate the raceway at a different time into an operable position relative to the peristaltic pump actuator.

In a seventy-ninth aspect of the present disclosure, which may be combined with any other aspect or portion thereof, the motorized mechanism includes a motor operable with a lead screw or a linear actuator.

In an eightieth aspect of the present disclosure, which may be combined with any other aspect or portion thereof, the motorized mechanism is configured to (i) translate the raceway away from the peristaltic pump actuator automatically when the door is opened and to translate the raceway into an operable position relative to the peristaltic pump actuator automatically when the door is closed or (ii) translate the raceway away from the peristaltic pump actuator and/or to translate the raceway at a different time into an operable position relative to the peristaltic pump actuator in response to at least one user interface input.

In an eighty-first aspect of the present disclosure, which may be combined with any other aspect or portion thereof, a dialysis machine operable with a disposable set having a peristaltic pumping tube includes an actuation surface for receiving the disposable set; a peristaltic pump actuator extending from the actuation surface, the peristaltic pump actuator operable with the peristaltic pumping tube; a raceway translatable along the actuation surface; a door configured to be opened and closed relative to the actuation surface; and a linkage or a motorized mechanism configured to (i) translate the raceway away from the peristaltic pump actuator for moving the peristaltic pumping tube into position against the peristaltic pump actuator and (ii) translate the raceway into an operable position relative to the peristaltic pumping tube.

In an eighty-second aspect of the present disclosure, which may be combined with any other aspect or portion thereof, the linkage is provided, and wherein the linkage is constructed and arranged such that (i) is performed when the door is opened and (ii) is performed when the door is closed.

In an eighty-third aspect of the present disclosure, which may be combined with any other aspect or portion thereof, the motorized mechanism is provided, and wherein the motorized mechanism is constructed and arranged such that (i) is performed automatically when the door is opened and (ii) is performed automatically when the door is closed.

In an eighty-fourth aspect of the present disclosure, which may be combined with any other aspect or portion thereof, the motorized mechanism is provided, and wherein at least one of (i) or (ii) is performed in response to a user interface input.

In an eighty-fifth aspect of the present disclosure, which may be combined with any other aspect or portion thereof, the motorized mechanism includes a motor operable with a lead screw or a linear actuator.

In an eighty-sixth aspect of the present disclosure, which may be combined with any other aspect or portion thereof, a medical fluid system includes a medical fluid pump actuator; a medical fluid carrying set including a flexible sheet; a temperature sensor positioned and arranged to sense a temperature of the medical fluid flowing through the medical fluid carrying set; a pressure sensor positioned and arranged to contact the flexible sheet when the medical fluid carrying set is loaded for operation with the medical fluid pump actuator; and a control unit configured to (i) precondition the flexible sheet for operation with the pressure sensor by causing the medical fluid pump actuator to apply pressure to the flexible sheet and (ii) use an output from the temperature sensor in a compensation algorithm that modifies an output from the pressure sensor.

In an eighty-seventh aspect of the present disclosure, which may be combined with any other aspect or portion thereof, the medical fluid pump actuator is a peristaltic pump actuator.

In an eighty-eighth aspect of the present disclosure, which may be combined with any other aspect or portion thereof, the pressure sensor is positioned such that the flexible sheet is placed under tension via contact with the pressure sensor when the medical fluid carrying set is loaded for operation with the medical fluid pump actuator.

In an eighty-ninth aspect of the present disclosure, which may be combined with any other aspect or portion thereof, the pressure sensor is operable with a pressure pod potion of the flexible sheet.

In a ninetieth aspect of the present disclosure, which may be combined with any other aspect or portion thereof, the pressure applied during (i) is fluid pressure.

In a ninety-first aspect of the present disclosure, which may be combined with any other aspect or portion thereof, the pressure applied during (i) is a cyclical up and down pressure.

In a ninety-second aspect of the present disclosure, which may be combined with any other aspect or portion thereof, the pressure applied during (i) is from 100% to 150% of a maximum operating pressure supplied during treatment.

In a ninety-third aspect of the present disclosure, which may be combined with any other aspect or portion thereof, the medical fluid system includes a plurality of valves operable with the medical fluid carrying set, and wherein the control unit causes the plurality of valves to be closed during (i).

In a ninety-fourth aspect of the present disclosure, which may be combined with any other aspect or portion thereof, the algorithm is $V_T = V_0 + gT$, wherein $V_0$ is the output from the pressure sensor, $V_T$ is a modified pressure output, g is a temperature scaling coefficient, and T is the sensed temperature.

In a ninety-fifth aspect of the present disclosure, which may be combined with any other aspect or portion thereof, the control unit is configured to update the compensation algorithm for temperature (i) each time the output from the pressure sensor is read by the control unit or (ii) on a periodic basis.

In a ninety-sixth aspect of the present disclosure, which may be combined with any other aspect or portion thereof, wherein the control unit is configured to use the modified output from the pressure sensor in (ii) for at least one of (a) controlling the medical fluid pump actuator to pump within a patient pressure limit, (b) determining a line occlusion condition or (c) determining a container empty condition.

In a ninety-seventh aspect of the present disclosure, which may be combined with any other aspect or portion thereof, a medical fluid system includes a medical fluid pump actuator; a medical fluid carrying set including a flexible sheet; a pressure sensor positioned such that the flexible sheet is placed under tension via contact with the pressure sensor when the medical fluid carrying set is loaded for operation with the medical fluid pump actuator; and a control unit configured to precondition the flexible sheet for operation with the pressure sensor by causing the medical fluid pump actuator to apply pressure to the flexible sheet.

In a ninety-eighth aspect of the present disclosure, which may be combined with any other aspect or portion thereof, the pressure applied during the preconditioning is fluid pressure.

In a ninety-ninth aspect of the present disclosure, which may be combined with any other aspect or portion thereof, the pressure applied during the preconditioning is a cyclical up and down pressure.

In a one-hundredth aspect of the present disclosure, which may be combined with any other aspect or portion thereof, the pressure applied during the preconditioning is from 100% to 150% of a maximum operating pressure supplied during treatment.

In a one-hundred-first aspect of the present disclosure, which may be combined with any other aspect or portion thereof, the medical fluid system includes a plurality of valves operable with the medical fluid carrying set, and wherein the control unit causes the plurality of valves to be closed during the preconditioning.

In a one-hundred-second aspect of the present disclosure, which may be combined with any other aspect or portion thereof, a medical fluid system includes a medical fluid pump actuator; a medical fluid carrying set including a flexible sheet; a temperature sensor positioned and arranged to sense a temperature of the medical fluid flowing through the medical fluid carrying set; a pressure sensor positioned such that the flexible sheet is placed under tension via contact with the pressure sensor when the medical fluid carrying set is loaded for operation with the medical fluid pump actuator; and a control unit configured to use an output from the temperature sensor in a compensation algorithm that modifies an output from the pressure sensor.

In a one-hundred-third aspect of the present disclosure, which may be combined with any other aspect or portion thereof, the control unit is configured to update the compensation algorithm for temperature (i) each time the output from the pressure sensor is read by the control unit or (ii) on a periodic basis.

In a one-hundred-fourth aspect of the present disclosure, which may be combined with any other aspect or portion thereof, the control unit is configured to use the modified output from the pressure sensor for at least one of (i) controlling the medical fluid pump actuator to pump within a patient pressure limit, (ii) determining a line occlusion condition or (iii) determining a container empty condition.

In a one-hundred-fifth aspect of the present disclosure, which may be combined with any other aspect or portion thereof, a dialysis machine operable with a disposable set having at least one container includes a pump actuator operable to pump dialysis fluid to and/or from the at least one container; a weigh plate positioned to support the at least one container; a plurality of operational load cells positioned to support the weigh plate; a linear actuator positioned to apply a force to the weigh plate; a calibration load cell positioned to measure the force applied by the linear actuator; and a control unit in operable communication with the operational load cells, the linear actuator and the calibration load cell, the control unit configured to cause the linear actuator to apply the force to the weigh plate, compare resulting outputs from the operational load cells and the calibration load cell, and determine a calibration factor from the comparison for offsetting future outputs from the operational load cells.

In a one-hundred-sixth aspect of the present disclosure, which may be combined with any other aspect or portion thereof, the operational load cells are positioned to be at least substantially equidistant from the center of mass of the weigh plate.

In a one-hundred-seventh aspect of the present disclosure, which may be combined with any other aspect or portion thereof, the calibration load cell is positioned to be at least substantially at the center of mass of the weigh plate.

In a one-hundred-eighth aspect of the present disclosure, which may be combined with any other aspect or portion thereof, the linear actuator includes a motor and lead screw or a linear stepper motor.

In a one-hundred-ninth aspect of the present disclosure, which may be combined with any other aspect or portion thereof, the linear actuator is positioned between the calibration load cell and the weigh plate.

In a one-hundred-tenth aspect of the present disclosure, which may be combined with any other aspect or portion thereof, the control unit is configured to sum the resulting outputs from the operational load cells for comparison to the resulting output from the calibration load cell.

In a one-hundred-eleventh aspect of the present disclosure, which may be combined with any other aspect or portion thereof, the calibration factor for offsetting the future outputs from the operational load cells is applied to the sum of the future outputs from the operational load cells.

In a one-hundred-twelfth aspect of the present disclosure, which may be combined with any other aspect or portion thereof, the calibration factor includes the resulting output from the calibration load cell divided by the sum of the resulting outputs from the operational load cells.

In a one-hundred-thirteenth aspect of the present disclosure, which may be combined with any other aspect or portion thereof, the linear actuator is in mechanical communication with the weigh plate, and wherein the control unit is configured to cause the linear actuator to apply a pulling force to the weigh plate.

In a one-hundred-fourteenth aspect of the present disclosure, which may be combined with any other aspect or portion thereof, the control unit is configured to cause the linear actuator to apply the force to the weigh plate prior to the container being placed on the weigh plate.

In a one-hundred-fifteenth aspect of the present disclosure, which may be combined with any other aspect or portion thereof, the control unit is configured to cause the linear actuator to apply the force to the weigh plate during treatment while the container is being supported by the weigh plate.

In a one-hundred-sixteenth aspect of the present disclosure, which may be combined with any other aspect or portion thereof, the control unit is in operable communication with the pump actuator, and wherein at least a duration of operation of the pump actuator is controlled using offsetted outputs from the operational load cells.

In a one-hundred-seventeenth aspect of the present disclosure, which may be combined with any other aspect or portion thereof, the control unit is configured to cause the linear actuator to not supply the force during the duration of operation.

In a one-hundred-eighteenth aspect of the present disclosure, which may be combined with any other aspect or portion thereof, the control unit is configured to use two or more offsetted outputs from the operational load cells to determine a mass or volumetric flowrate during treatment.

In a one-hundred-nineteenth aspect of the present disclosure, which may be combined with any other aspect or portion thereof, a dialysis system includes a disposable set including a pumping portion and at least one container; and a dialysis machine including a pump actuator operable with the pumping portion to pump dialysis fluid to and/or from the at least one supply container, a weigh plate positioned to support the at least one container, a plurality of operational load cells positioned to support the weigh plate, a linear actuator positioned to apply a force to the weigh plate, a calibration load cell positioned to measure the force applied by the linear actuator, and a control unit in operable communication with the operational load cells, the linear actuator and the calibration load cell, the control unit configured to cause the linear actuator to apply the force to the weigh plate, compare resulting outputs from the operational load cells and the calibration load cell, and determine a calibration factor from the comparison for offsetting future outputs from the operational load cells.

In a one-hundred-twentieth aspect of the present disclosure, which may be combined with any other aspect or portion thereof, the control unit is configured to sum the resulting outputs from the operational load cells for comparison to the resulting output from the calibration load cell.

In a one-hundred-twenty-first aspect of the present disclosure, which may be combined with any other aspect or portion thereof, the calibration factor for offsetting the resulting outputs from the operational load cells is applied to the sum of the resulting outputs from the operational load cells.

In a one-hundred-twenty-second aspect of the present disclosure, which may be combined with any other aspect or portion thereof, the at least one container includes at least one supply container, the pump actuator is operable with the pumping portion to pump fresh dialysis from the at least one supply container, and the control unit is configured to determine an amount of fresh dialysis fluid delivered using at least two offsetted outputs from the operational load cells.

In a one-hundred-twenty-third aspect of the present disclosure, which may be combined with any other aspect or portion thereof, the at least one container includes at least one drain container, the pump actuator is operable with the pumping portion to pump used dialysis to the at least one drain container, and the control unit is configured to determine an amount of used dialysis fluid delivered using at least two offsetted outputs from the operational load cells.

In a one-hundred-twenty-fourth aspect of the present disclosure, which may be combined with any other aspect or portion thereof, the control unit is configured to determine an amount of fresh dialysis fluid delivered to, or used dialysis fluid removed from, a patient using at least two offsetted outputs from the operational load cells.

In a one-hundred-twenty-fifth aspect of the present disclosure, any of the features, functionality and alternatives described in connection with any one or more of FIGS. 1 to 13 may be combined with any of the features, functionality and alternatives described in connection with any other of FIGS. 1 to 13 and/or any of the aspects listed herein.

It is accordingly an advantage of the present disclosure to provide an accurate APD system that uses a relatively simple and cost effective peristaltic pump.

It is another advantage of the present disclosure to provide an APD system that eliminates certain sealing issues present in known APD systems.

It is a further advantage of the present disclosure to provide an APD pump driven system that eliminates bulky pneumatic equipment associated with certain APD systems.

It is yet another advantage of the present disclosure to provide an APD pump driven system that reduces noise relative to pneumatic systems.

It is yet a further advantage of the present disclosure to provide an APD system that manages peritoneal dialysis fluid flow so as to be within safe and comfortable patient pressure limits.

It is still another advantage of the present disclosure to provide an APD system having a simplified disposable set.

It is still a further advantage of the present disclosure to provide an APD system having accurate pressure and weight sensing.

Moreover, it is an advantage of the present disclosure to provide an APD system that simplifies used dialysis fluid removal to house drain for the patient.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE DRAWINGS

FIG. 4 is an elevation view of one embodiment of a pinch valve of the present disclosure.

FIGS. 5A and 5B are elevation and sectioned views, respectively, of one embodiment of sprung end effector valve plunger of the present disclosure.

DETAILED DESCRIPTION

System Overview

Figure 1:
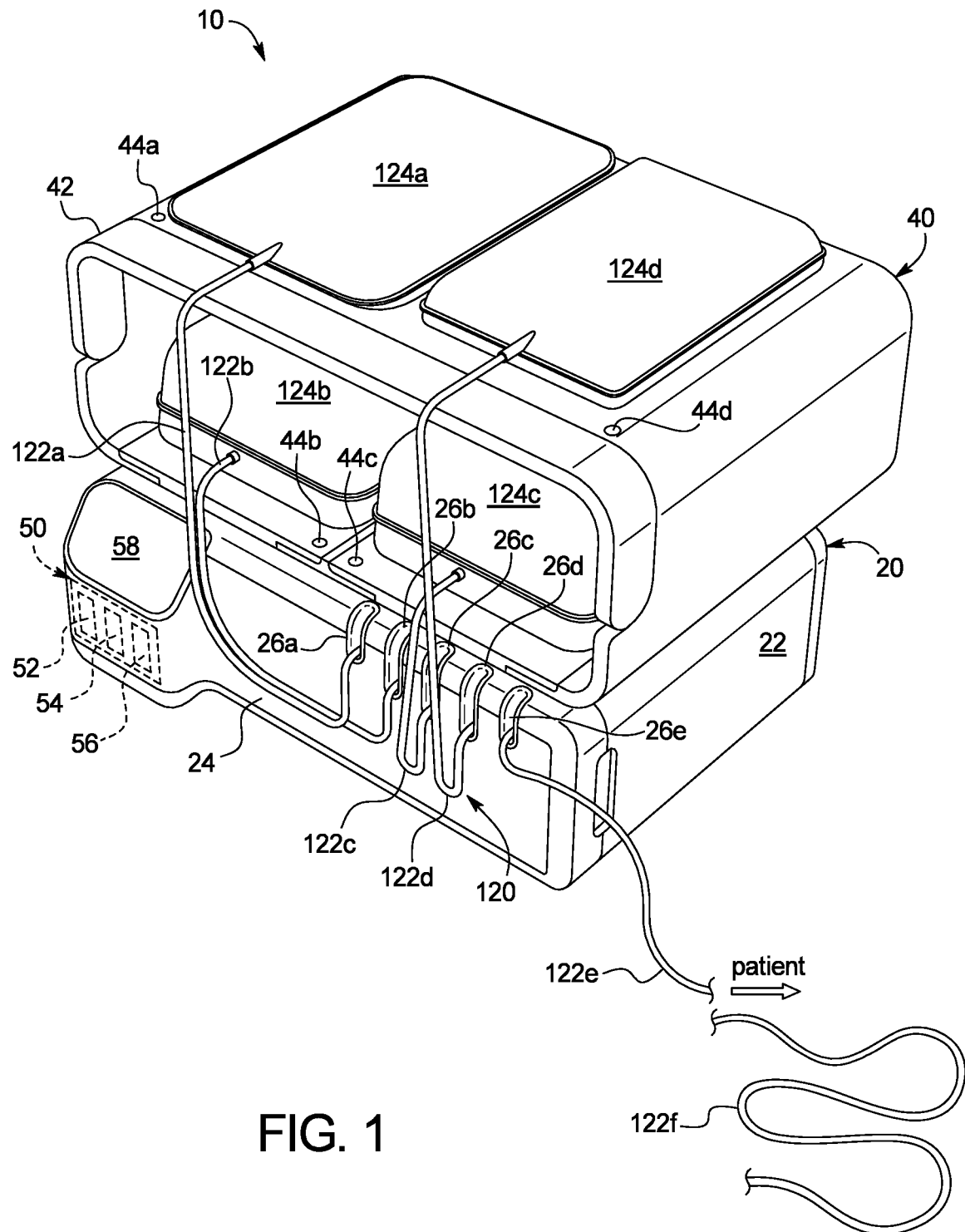
FIG. 1 is a perspective view of one embodiment of a system and associated cycler and disposable set of the present disclosure.

Referring now to the drawings and in particular to FIG. 1, an embodiment of system 10 includes an automated peritoneal dialysis ("APD") cycler 20 having a housing 22, which uses peristaltic pumping in one embodiment, and which operates a disposable set 120. All rigid and flexible tubing portions of disposable set 120 may be made of one or more plastic, e.g., polyvinylchloride ("PVC") or a non-PVC material, such as polyethylene ("PE"), polyurethane ("PU") or polycarbonate ("PC"). Housing 22 of cycler 20 may be made of any of the above plastics, and/or of metal, e.g., stainless steel, steel and/or aluminum.

In the illustrated embodiment, housing 22 is provided with hinged door 24 having a series of holes or slots 26a, 26b, 26c, 26d and 26e for tubing 122a to 122e, respectively, of disposable set 120 to extend from the inside of housing 22 to the outside of the housing. While illustrated as elongated slots, the apertures 26a to 26e may alternatively be holes. Slots 26a to 26e are advantageous however because they allow door 22 to be hinged open without placing tubing 122a to 122e under too much tension. In an embodiment, tubing 122a to 122e is preconnected and sterilized with a disposable pumping cassette illustrated below. The distal ends of tubing 122a to 122e are removed from sterilized caps at treatment setup and spiked to containers or bags 124a to 124d (line 122e is the patient line) of disposable set 120. Container or bag 124a may be a drain container or bag. Containers or bags 124b and 124c may be primary fresh dialysis fluid supply containers or bags. Container 124d may be a last fill container or bag, which holds a different formulation of fresh dialysis fluid, e.g., two to three liters of icodextrin, which is formulated to remain inside the patient's peritoneal cavity after the patient disconnects from disposable set 120.

In the illustrated embodiment, door 24 is vertically disposed and thus holds the disposable cassette of set 120 vertically within housing 22 of cycler 20 and against an actuation surface of the housing. Door 24 is located adjacent to a user interface portion of cycler 20, which includes a control unit 50 having one or more processor 52, one or more memory 54 and a video controller 56, which interfaces one or more processor 52 and one or more memory 54 with a user interface 58. User interface 58 may include a touch screen and/or electromechanical buttons, such as membrane switches for inputting user commands and providing instructions, alerts and alarms. Providing user interface 58 next to door 24 of housing 22 enables the patient or other user to generally interact with one surface of machine 20 for inputting commands, receiving data and loading/unloading the disposable cassette. User interface 58 may alternatively or additionally be a remote user interface, e.g., via a tablet or smartphone. Control unit 50 may also include a transceiver and a wired or wireless connection to a network (not illustrated), e.g., the internet, for sending treatment data to and receiving prescription instructions/changes from a doctor's or clinician's server interfacing with a doctor's or clinician's computer. The data sent to the doctor's or clinician's computer may be analyzed and/or converted to, or used to form, other data useful for analysis. Such data conversion is performed alternatively or additionally at control unit 50 of cycler 20.

FIG. 1 illustrates that system 10 in one embodiment also includes a bag shelf enclosure 40 that serves multiple purposes. Bag shelf enclosure 40 is sized such that when cycler 20 is not in use, the cycler may be stored inside of the enclosure. In the illustrated embodiment, bag shelf enclosure 40 includes a rotatably hinged handle 42 that enables the user to transport the enclosure with cycler 20 stored therein. As illustrated in FIG. 1, bag shelf enclosure 40 is also sized such that when cycler 20 is in use, the bag shelf enclosure may be set on the top of the cycler (on top of a weigh plate in one embodiment as discussed in detail below). Bag shelf holds multiple containers or bags 124a to 124d, such as multiple supply containers 124b to 124d and one or more drain container 124a. As illustrated, the containers or bags are held within enclosure 40 and on the outer, upper surface of the enclosure.

Bag shelf enclosure 40 may include color-coded markers 44a to 44d provided at locations for loading containers or bags having lines that extend into cycler 20 through slots or apertures, 26a to 26d, wherein the slots or apertures have like color-coded markers or borders. The matching color-coded markers 44a to 44d and slot borders make it easy for the patient or caregiver to identify which bag and line belongs at which location on bag shelf enclosure 40. For instance, marker 44a and the border of slot 26a may be green to signify drain line 122a and drain container 124a and the desired location for the drain container. Markers 44b and 44c and the borders of slots 26b and 26c may be blue to signify primary supply lines 122b, 122c and supply containers 124b, 124c and the desired locations of the supply containers. Marker 44d and the border of slot 26d may be red to signify last fill line 122d and last fill container 124d and the desired location for the last fill container.

Drain/Purge

It is contemplated to use the supply containers or bags, e.g., the primary supply containers or bags 124b and 124c later as drain containers or bags to reduce overall disposable cost. For example, assume that the patient is full of effluent at the beginning of treatment. That effluent is initially drained from the patient and delivered to initially empty drain container 124a. A first patient fill is then delivered from a first primary supply container 124b to the patient, and after a specified dwell period delivered to the same drain container 124a (or perhaps to a different drain container depending on the sizes of the drain container(s)). In an embodiment, drain container 124a and primary supply containers 124b and 124c are larger, six liter, containers for holding multiple cycles' worth of fresh and used dialysis fluid. Drain container(s) 124a is/are used to receive effluent until first supply container 124b is emptied after which the first supply container receives effluent after a dwell period using PD fluid provided from second supply container 124c. First supply container 124b is used to receive patient effluent, perhaps over multiple patient fills, dwells and drains, until second supply container 124c is empty. At that point the patient may receive a last fill of a different formulation of peritoneal dialysis fluid from last fill container 124d, which remains within the patient until the next night treatment or perhaps until a midday exchange. If second supply container 124c is empty at the end of treatment, it may be used as the initial empty drain container at the start of the next treatment, further reducing disposable waste and cost.

In an example, containers 124a to 124d may be used as follows where the patient is initially full:
  initial drain→drain container 124a
  supply container 124b→first fill→drain container 124a
  supply container 124b→second fill→drain container 124a
  supply container 124c→third fill→supply container 124b
  supply container 124c→fourth fill→supply container 124b
  last fill container 124d—last fill In an example, containers 124a to 124d may be used as follows where the patient is initially empty:
  supply container 124b→first fill→drain container 124a
  supply container 124b→second fill→drain container 124a
  supply container 124c→third fill→supply container 124b
  supply container 124c→fourth fill→supply container 124b
  last fill container 124d—last fill At the end of treatment, multiple containers or bags (e.g., containers 124a, 124b) are full of effluent. Also, a remaining supply container 124c may contain residual fresh dialysis fluid. To prevent the patient or caregiver from having to transport the full drain bags to a house drain, e.g., toilet, sink or bathtub, control unit 50 of cycler 20 is programed to prompt the user to remove patient line 122e from the patient's transfer set and carry the distal end of patient line 122e to the house drain. If needed, a reusable extension line 122f may be connected to the distal end of patient line 122e to reach the house drain. The patient or caregiver then presses a drain button on user interface 58, upon which cycler 20 actuates the pump actuator, e.g., peristaltic pump actuator, in a direction so as to pull used dialysis fluid or effluent from each of the drain containers 124a, 124b (one or more of which may be former supply containers) and pump the used dialysis fluid through patient line 122e (and extension line 122f if needed) to the house drain. Residual fresh dialysis fluid is removed from supply container 124c in the same way. The drain button in an embodiment is only displayed at the end of treatment, e.g., via a touch screen display, when the button is needed. The drain button may alternatively be a membrane switch that is only enabled at the end of treatment when the button is needed. Additionally, regardless of its type, the drain button may only be displayed and/or enabled after the patient presses a confirm button provide by user interface 58 in response to a prompt by the user interface for the patient or caregiver to confirm that patient line 122e/122f has been run to the house drain.

Control unit 50 of cycler 20 detects when each drain container 124a, 124b is empty (e.g., via a weigh scale and/or pressure sensor operating with a pressure pod of the disposable cassette as discussed in detail below) and automatically switches valve actuators, e.g., pinch valve actuators, to sequence between drain containers 124a, 124b (and supply container 124c if needed) until each is emptied. In particular, cycler 20 includes a patient valve actuator that operates with a patient valve seat provided by disposable set 120, and a drain valve actuator that operates with a drain valve seat provided by the disposable set, and wherein control unit 50 is configured to cause the patient valve actuator and the drain valve actuator to allow flow through the drain valve seat and the patient valve seat to pump the used dialysis fluid from the drain container, through the patient line, to the house drain. It should be appreciated that multiple drain containers (one or more of which may be former supply containers) may be drained simultaneously, over the same duration or overlapping durations, e.g., to save time.

It is also contemplated for control unit 50 to look for leftover fresh dialysis fluid in any remaining supply container, e.g., containers 124c and 124d, and to cause the pump actuator to pump the leftover fresh dialysis fluid to house drain via the patient line. In this manner, once the patient disconnects from patient line 122e and presses the drain button, the patient can assume that all fresh and used dialysis fluid is being pumped to house drain and is thus free to begin his or her day.

It should be appreciated that while system 10 is described in this section as pumping effluent or leftover fresh dialysis fluid to a house drain, control unit 50 may in an alternative embodiment pump any remaining fluid (fresh or used) from any container 124a to 124d to any other container 124a to 124d. In an embodiment, after treatment when the patient disconnects from patient line 122e, the patient places the distal end of the patient line in a priming holder (not illustrated) located on the housing 22 of cycler 20 and confirms this action at user interface 58. The distal end of patient line 122e is left open to atmosphere. Control unit 50 then runs a sequence in which all fluid currently residing in patient line 122e is pumped to a desired destination container 124a to 124d so that patient line 122e is completely or almost completely filled with air. Control unit 50 then causes whatever dialysis fluid (fresh or used) is to be moved from whatever container 124a to 124d to be pumped via peristaltic pump actuator 60, rotating in a patient fill direction for a known number of strokes, to push an amount of the fluid through inline fluid heating pathway 144 and into a safe portion of patient line 122e, so that the fluid does not spill out the end of the patient line. Control unit 50 then reverses the direction of peristaltic pump actuator 60 so as to rotate in a patient drain direction, for a known number of strokes, and changes the valve states of the relevant valve actuators, to push that amount of the fluid through the safe portion of patient line 122e and inline fluid heating pathway 144 to a desired destination container 124a to 124d. Control unit 50 then repeats the pumping and reverse pumping actions until a desired amount of fresh or used dialysis fluid is moved from a desired source container 124a to 124d to a desired destination container 124a to 124d.

Autoloader

Figure 2:
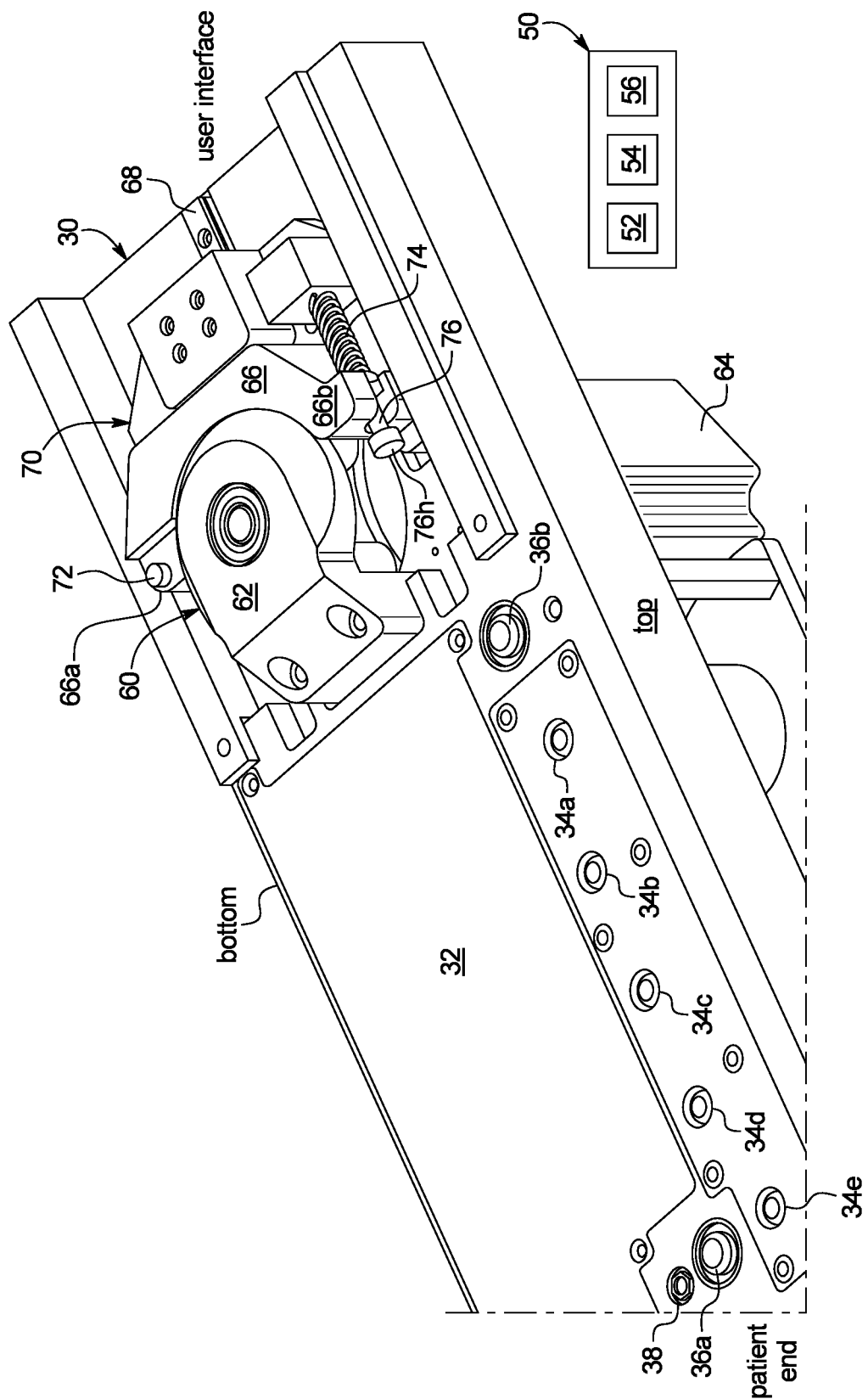
FIG. 2 is a perspective view of one embodiment of an actuation surface of the cycler of the present disclosure.

Referring now to FIG. 2, one embodiment for actuation surface 30 of cycler 32 is illustrated. Actuation surface 30 in FIG. 1 is hidden behind door 24. When door 24 is opened, actuation surface 30 as illustrated in FIG. 2 is exposed. Labels "top", "bottom", "user interface" and "patient end" are provided in FIG. 2 to illustrate how actuation surface 30 is oriented in FIG. 1. Actuation surface 30 in the illustrated embodiment includes a heater 32, such as a resistive plate that heats an inline fluid heating pathway provided by the disposable cassette illustrated below. Actuation surface 30 also includes a plurality of valve actuators 34a to 34e, including a drain line valve actuator 34a, main supply line valve actuators 34b and 34c, last fill line valve actuator 34d and patient line valve actuator 34e. An embodiment for valve actuators 34a to 34e is illustrated in detail below. Actuation surface 30 also includes a plurality of pressure sensors, including a patient pressure sensor 36a and a pumping pressure sensor 36b. An embodiment for pressure sensors 36a and 36b is likewise illustrated in detail below. At least one temperature sensor 38, e.g., thermocouple or thermistor, is also provided. Control unit 50 shown figuratively in FIG. 2 controls heater 32 and valve actuators 34a to 34e and receives inputs from pressure sensors 36a, 36b and temperature sensor 38.

FIG. 2 further illustrates that a peristaltic pump actuator 60 under control of control unit 50 is located on and extends behind actuation surface 30 of cycler 20. Pump actuator 60 may include a pump head 62 located on actuation surface 30 and a driver or motor 64 located behind actuation surface 30. The disposable cassette includes a peristaltic pump tube that the user guides over pump head 62 of peristaltic pump actuator 60 when loading the cassette. In operation, peristaltic pump actuator 60 compresses the peristaltic pump tube at multiple points against a raceway 66. The operational proximity of raceway 66 to peristaltic pump actuator 60 would make the loading of the tube difficult. The present cycler 20 accordingly provides a moveable raceway 66 that translates out of the way of the peristaltic pump actuator, for example, via a linkage (not illustrated) when the patient or caregiver opens door 24 of cycler 20 to load the disposable cassette. After the cassette is loaded, the closing of cycler door 24 causes moveable raceway 66 to translate, for example, via the linkage into operable position directly adjacent to the peristaltic pump tube. In an alternative embodiment, a motor and lead screw assembly, or a linear actuator (e.g., linear stepper motor, not illustrated) is provided to automatically translate raceway 66 out of the way of peristaltic pump actuator 60 when the patient or caregiver opens door 24 to load the cassette and to automatically translate raceway 66 into an operable position when door 24 is closed. In a further alternative embodiment, motor and lead screw assembly, or a linear actuator (e.g., linear stepper motor, not illustrated) is provided, but the patient or caregiver instead presses one or more button on the user interface 58 to translate raceway 66 out of the way or into the operable position.

In an embodiment, raceway 66 is mounted to a block or member 70 that is translatable across actuation surface 30 towards and away from peristaltic pump actuator 60. Besides the translatable motion of member 70 (and raceway 66), moveable raceway 66 is also able to rotate about a pivot 72 provided at one end 66a of raceway 66, wherein pivot 72 is mounted to translatable member 70. The other end 66b of raceway 66 is spring-loaded via a spring 74, e.g., compression spring, confined between raceway end 66b and member 70. In the illustrated embodiment, spring 74 is inserted over a threaded bolt 76 that extends through raceway end 66b and threads into member 70. Threaded bolt 76 incudes a head 76h that sets and end of spring travel for raceway 66, wherein the end of travel may be adjusted in or out by turning threaded bolt 76 clockwise or counterclockwise, respectively. In the illustrated embodiment, spring 74 pushes raceway 66 about pivot 72 and into a desirable operating position around the peristaltic pumping tube after member 76 has been translated towards peristaltic pump actuator 60. Pivoting raceway 66 absorbs or allows for variances due to tubing tolerance and may also provide a dampening effect that aids noise reduction.

Figure 3:
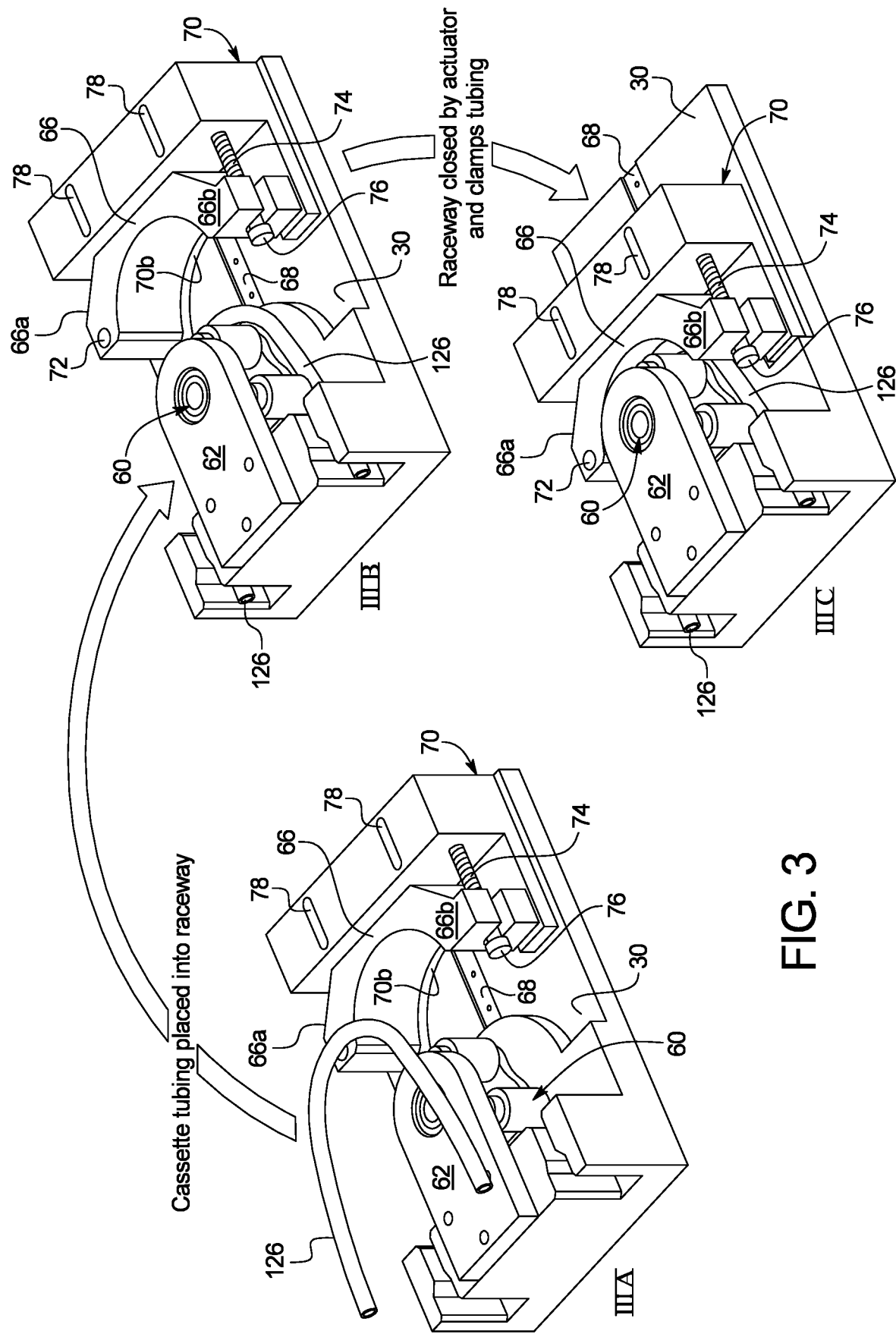
FIG. 3 is a perspective view of one embodiment of a peristaltic pump tubing autoloading structure and associated functionality.

FIGS. 2 and 3 illustrate that member 70 and raceway 66 slide along a linear rail 68 formed or provided along actuation surface 30. Member 70 on its underside includes a rail receiver (not viewable) sized to fit and operate with the linear rail 68. The rail receiver in an embodiment interacts with linear rail 68, e.g., via a tongue and groove fit, such that linear rail 68 holds member 70 and raceway 66 slidingly engaged along actuation surface 30. Additionally or alternatively, FIG. 3 illustrates that elongated slots 78 may be formed in member 70, which receive bolts that may be loosely tightened such that member 70 and raceway 66 may slide along actuation surface 30 while still being held to the surface.

Section IIIA of FIG. 3 illustrates peristaltic pumping tube 126 of disposable set 120 as it is about to be loaded. Member 70 and raceway 66 are in a fully retracted or out of the way position. Section IIIB of FIG. 3 illustrates that peristaltic pumping tube 126 has been stretched or placed into operable position about pump head 62 of peristaltic pump actuator 60. Member 70 and raceway 66 are again in a fully retracted or out of the way position. Section IIIC of FIG. 3 illustrates that member 70 and raceway 66 have been translated into an operable position relative to peristaltic pumping tube 126 and pump head 62 of peristaltic pump actuator 60.

As mentioned above, a purely mechanical linkage (not illustrated) may be provided that pulls member 70 and raceway 66 into the fully retracted or out of the way position of sections IIIA and IIIB of FIG. 3, e.g., wherein the linkage is actuated via the opening of door 24. The linkage pushes member 70 and raceway 66 into the operable position of section IIIC of FIG. 3, e.g., wherein the linkage is actuated via the closing of door 24. Alternatively a motorized mechanism, such as a linear actuator or motor and lead screw, are provided to automatically (i) pull member 70 and raceway 66 into the fully retracted or out of the way position of sections IIIA and IIIB of FIG. 3 when door 24 is opened and (ii) push member 70 and raceway 66 into the operable position of section IIIC of FIG. 3 when door 24 is closed. Further alternatively, if it is desirable to be able to access actuation surface 30 when member 70 and raceway 66 are in the operable position, a button may be provided on user interface 58 to actuate the motorized mechanism, e.g., to both retract and extend member 70 and raceway 66 or perhaps only to extend member 70 and raceway 66 into the operable position after they have been pulled into the fully retracted position automatically upon opening door 24. Control unit 50 may be programmed to perform any of such sequences.

As illustrated in the fully retracted sections IIIA and IIIB of FIG. 3, member 70 includes a base 70b that defines an arc having a radius that at least substantially matches a radius of raceway 66. It is contemplated that head 76h of bolt 76 provides a stop that is positioned (e.g., via threading bolt 76 into our out of member 70) to stop a pivoting of raceway 66 caused via spring 74 when the radius of raceway 66 at least substantially reaches and thus matches the radius of the arc of base 70b. As mentioned above, raceway 66 is moveable primarily to allow ease of loading. A secondary benefit of the translational motion is the adjustment of the raceway position to optimize for tubing variability. Pivoting via pivot 72 and spring 74 helps to absorb tubing tolerance and provides a dampening effect which aids noise reduction. It should be appreciated that while spring 74 is illustrated as a compression spring, the spring may alternatively be a tension spring or other type of spring.

Sprung End Effector

Referring now to FIGS. 4, 5A and 5B, an embodiment for any or all of pinch valve actuators 34a to 34e is illustrated. Disposable cassette 130, e.g., injection or blow molded plastic, is provided with valve seats 132a to 132e that receive pinch valve actuators 34a to 34e, respectively, to occlude or close a fluid pathway 134 provided by the disposable cassette. In FIG. 4, disposable cassette 130 is sealed to, e.g., ultrasonically welded, heat sealed and/or solvent bonded, and covered by a flexible sheet 136, e.g., flexible plastic, portions of which pinch valve actuators 34a to 34e press into respective valve seats 132a to 132e to close a respective fluid pathway 134. Pinch valve actuators 34a to 34e retract to open respective fluid pathways 134. As illustrated in FIG. 4, an opening in valve seats 132a to 132e extends through a rigid body 138 of disposable cassette 130 and through a port 140a to 140e extending in the opposite direction from the valve seats. A respective line or tube 122a to 122e is connected sealingly, e.g., ultrasonically welded, heat sealed and/or solvent bonded, respectively to port 140a to 140e. Line or tube 122a to 122e extends from disposable cassette 130 out through door 24 via a respective slot or aperture 26a to 26e as illustrated in FIG. 1.

As illustrated in FIG. 4, pinch valves 34a to 34e are each driven by a linear actuator 80, which may be any suitable type of linear actuator, such as a linear stepper motor, which under control of control unit 50 provides a necessary amount of travel (e.g., up to 10 mm) and a needed amount of pressurized cassette sheeting closing force (e.g., 30 to 60 Newtons ("N") or less). In the illustrated embodiment, linear actuator 80 is mounted to an internal wall 46 or other internal structure inside housing 22 of cycler 20, so that a valve plunger 84 connected to an output shaft 82 of linear actuator 80 extends through a hole 30h in actuation surface 30 so as to just meet a flexible valve membrane 48, e.g., flexible silicone, which is bolted in place against actuation surface 30. Linear actuator 80 drives valve plunger 84 to press flexible membrane 48 and a portion of cassette sheeting 136 against a respective cassette valve seat 132a to 132e. Linear actuator 80 retracts valve plunger 84 to allow the sheeting to be removed from, e.g., via its own resiliency and positive fluid pressure, a respective cassette valve seat 132a to 132e.

As illustrated in FIGS. 5A and 5B, valve plunger 84 in one embodiment includes a proximal end effector 86 that couples to linear actuator 80 and a distal end effector 90 that is slidingly coupled to proximal end effector 86. As illustrated in FIG. 5B, proximal end effector 86 includes a larger diameter portion 86a and a smaller diameter portion 86b. Distal end effector 90 includes or defines a cylindrical opening 92 that slidingly receives smaller diameter portion 86b of proximal end effector 86. In the illustrated embodiment, a spring 98 is positioned between a step 86c transitioning between the larger and smaller diameter portions

86a, 86b and a proximal edge 90p of distal end effector 90. Spring 98 extends over is accordingly constrained by smaller diameter portion 86b of proximal end effector 86. FIGS. 5A and 5B illustrate that an outer diameter of the distal end effector 90 may be at least substantially equal to that of larger diameter portion 86a of proximal end effector 86.

One of proximal end effector 86 or distal end effector 90 defines at least one groove and the other of the proximal end effector or the distal end effector includes at least one spring arm that mechanically fits, e.g., snap-fits, into the at least one groove to slideably attach the end effectors together. In the illustrated embodiment, proximal end effector 86 defines at least one groove 88, while distal end effector 90 includes or defines a plurality of spring arms 94a, 94b . . . 94n, that mechanically fit, e.g., snap-fit, into the at least one groove 88. If it is desirable for distal end effector 90 not to spin relative to proximal end effector 86, then a separate groove 88 may be defined for each spring arm 94a, 94b . . . 94n. If it does not matter, then a single, annular groove 88 may be provided instead. In any case, the length of at least one groove 88 is sized to provide a length of travel of distal end effector 90 relative to proximal end effector 86, which is equal to or greater than an uncompressed length of spring 98.

Spring 98 may be a wave or a compression spring. One acceptable length of travel for spring 98 is 2.9 mm. In an embodiment, spring 98 is configured to provide a 25 N sealing force needed to seal cassette sheeting 136 properly against valve seats 132a to 132e after about 1.4 mm of compression travel. Spring 98 may at solid length exert a force up to 51 N, wherein linear actuator 80 is selected to have an at east slightly higher peak force.

Spring 98 is positioned so as to bias distal end effector 90 outwardly relative to the proximal end effector 86. The variable distance provided by spring 98 enables pinch valve 34a to 34e to contact cassette sheeting 136 (via flexible membrane 48) initially at a lesser closing force, which increases steadily as spring 98 is compressed. Flexible membrane 48 is fixed to actuation surface 30 so as to cover the end of distal end effector 90. When spring 98 is fully compressed, cassette sheeting 136 and valve seat 132a to 132e see the full closing force of linear actuator 80 and spring 98. Spring 198 accordingly provides a force buffer that helps to protect flexible membrane 48 over multiple treatments and cassette sheeting 136 over a single treatment. Spring 98 may also help with variances due to tolerance in disposable cassette 130 and the loading thereof, and may further allow for a smaller or less expensive linear actuator 80.

Disposable Cassette/Valve Seat

Figure 7:
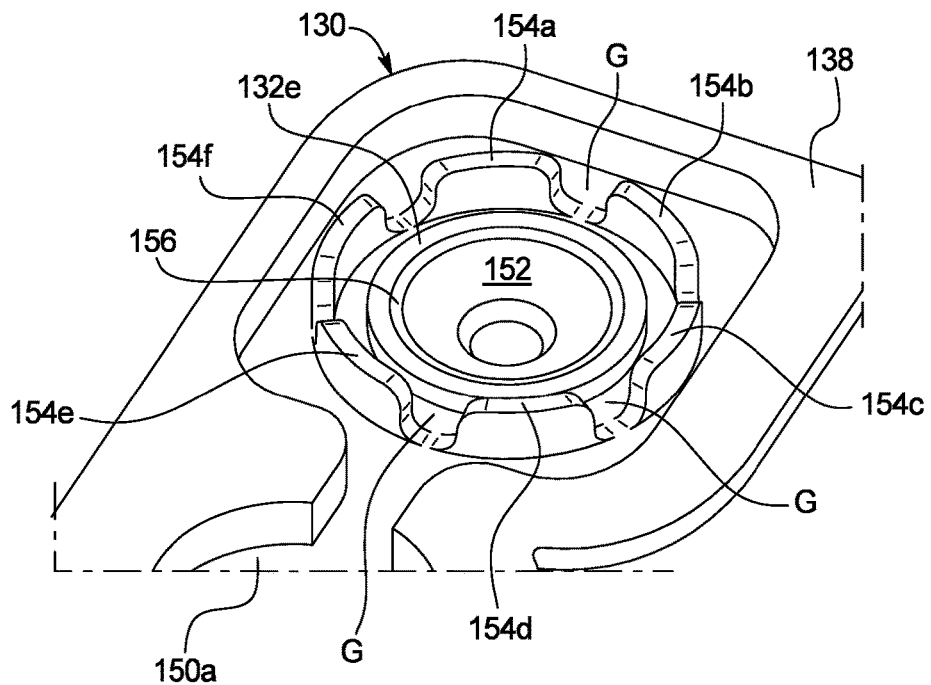
FIG. 7 is a perspective view of one embodiment for a valve seat of the present disclosure taken along line VII-VII in FIG. 6.
Figure 8:
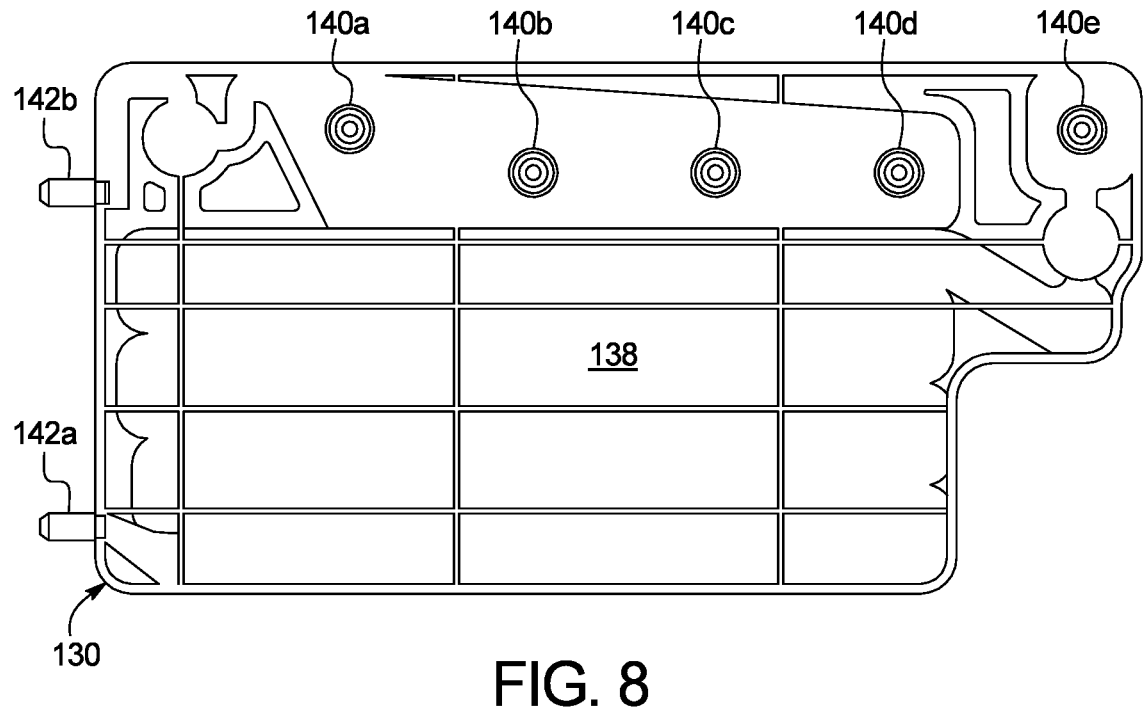
FIG. 8 is an elevation view of a side of one embodiment for the disposable cassette of the present disclosure that is viewed from the outside of the cycler when the disposable cassette is loaded for operation.
Figure 9:
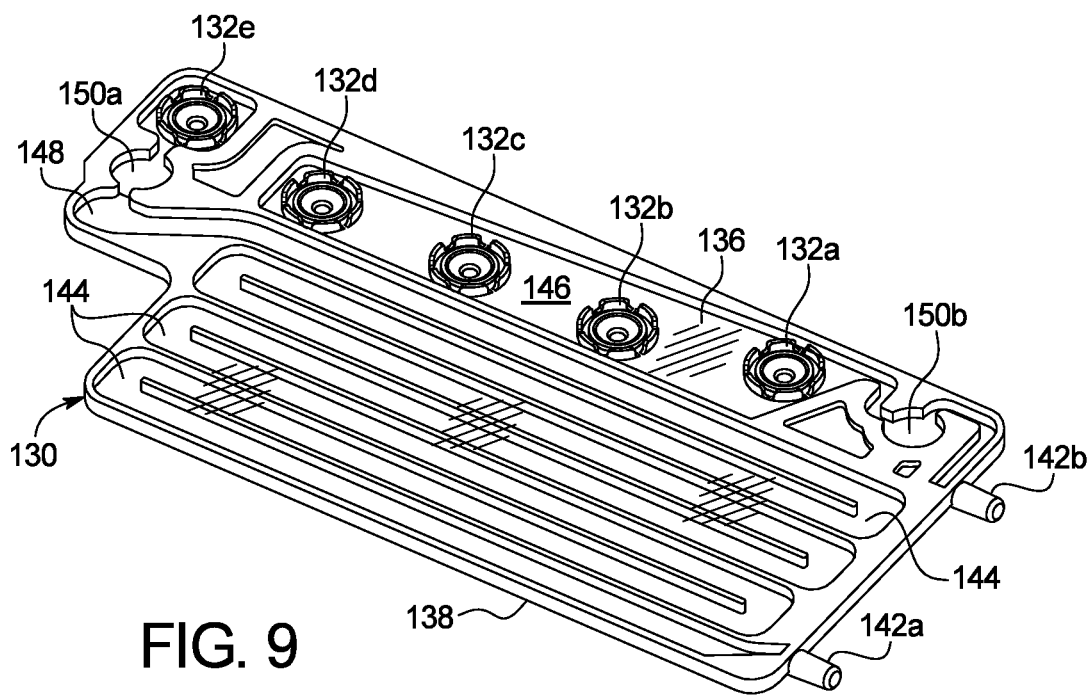
FIG. 9 is a perspective view of the operational side of one embodiment for the disposable cassette of the present disclosure showing how fluid pathways and valve seats are formed.

Referring now to FIGS. 6 to 10, disposable cassette 130 in the illustrated embodiment provides multiple valves seats, which may include a patient line valve seat 132e, first and second supply line valve seats 132b, 132c, a last fill line valve seat 132d and a drain line valve seat 132a. In the illustrated embodiment of FIGS. 6 and 9, patient line valve seat 132e is separated fluidically from a first peristaltic tube port 142a by an inline fluid heating pathway 144, e.g., a serpentine pathway. When disposable cassette 130 is mounted for operation, inline fluid heating pathway 144 is abutted against heater 32, such as a resistive plate heater, illustrated in FIG. 2. FIG. 9 illustrates that flexible sheet 136 is sealed to rigid body 138 so as to cover fluid heating pathway 144, allowing heat to be transferred through the thin-walled sheeting to fresh dialysis fluid traveling through the pathway.

Figure 6:
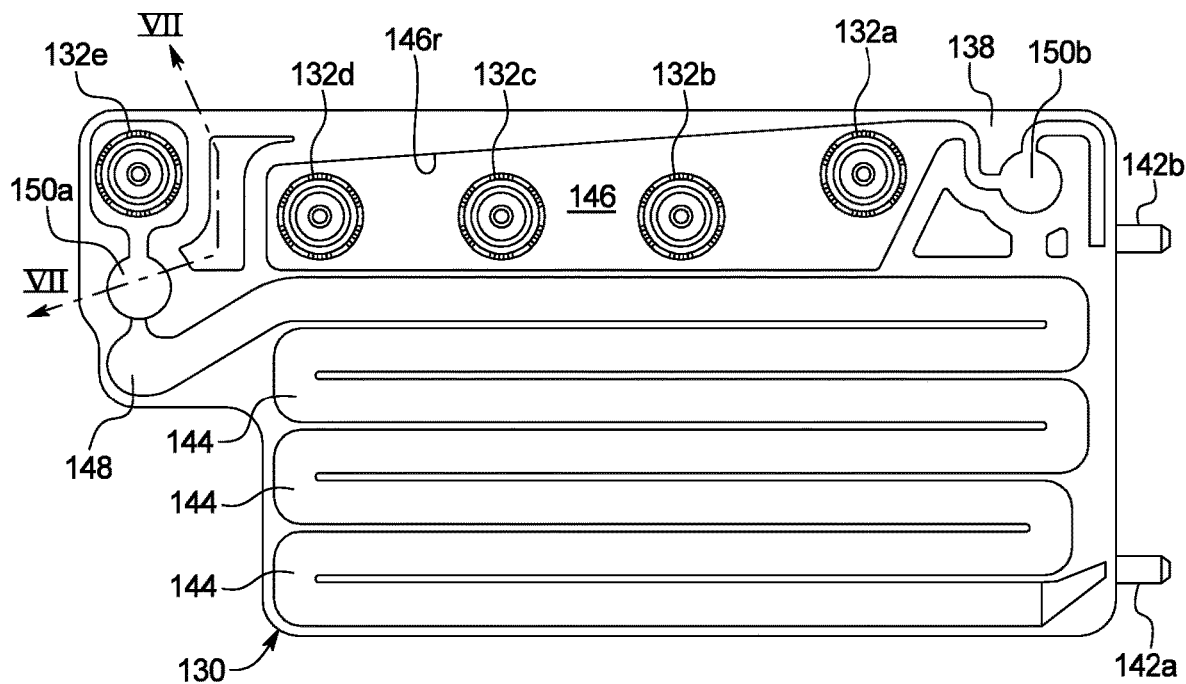
FIG. 6 is an elevation view of a side of one embodiment for a disposable cassette of the present disclosure that abuts against an actuation surface of the cycler.

FIGS. 6 and 9 illustrate that in one embodiment, first and second supply line valve seats 132b, 132c, last fill line valve seat 132d and a drain line valve seat 132a are each located within a common well 146, which is in fluid communication with a second peristaltic tube port 142b. Peristaltic pumping tube 126 is attached, e.g., ultrasonically welded, heat sealed and/or solvent bonded, to tube ports 142a and 142b. Fresh dialysis fluid may accordingly be pumped from any of the supply containers 124b to 124d for the first and second supply line valve seats 132b, 132c or the last fill line valve seat 132d in a first direction through common well 146 and inline fluid heating pathway 144, where the fresh dialysis fluid is heated, and then out the patient line valve seat 132e to the patient. Used dialysis fluid or effluent may be pumped from the patient in a second direction through the patient line valve seat 132e and inline fluid heating pathway 144, where the used dialysis fluid is not heated, into the common well 146 and out drain line valve seat 132a to drain container 124a.

Common well 146 simplifies the fluid pathways for cassette 130. Drain line valve seat 132a is placed closest to peristaltic tube port 142b so that used dialysis fluid travels a minimum distance within well 146 before reaching the drain line valve seat. FIG. 8, illustrating the non-operational side of disposable cassette 130, shows drain port 140a, supply container ports 140b, 140c, and last fill container port 140d extending from rigid body 138 on the other side from common well 146. Again, drain port 140a, to which drain line 122a is ultrasonically welded, heat sealed and/or solvent bonded, is located directly adjacent to peristaltic tube port 142b, so that used dialysis fluid is removed from common well 146 as quickly as possible to mitigate mixing with residual fresh dialysis fluid within the well. Supply container lines 122b, 122c, last fill container line 122d and patient line 122e are likewise ultrasonically welded, heat sealed and/or solvent bonded to supply container ports 140b, 140c, last fill container port 140d port and patient line port 140e, respectively.

Figure 10:
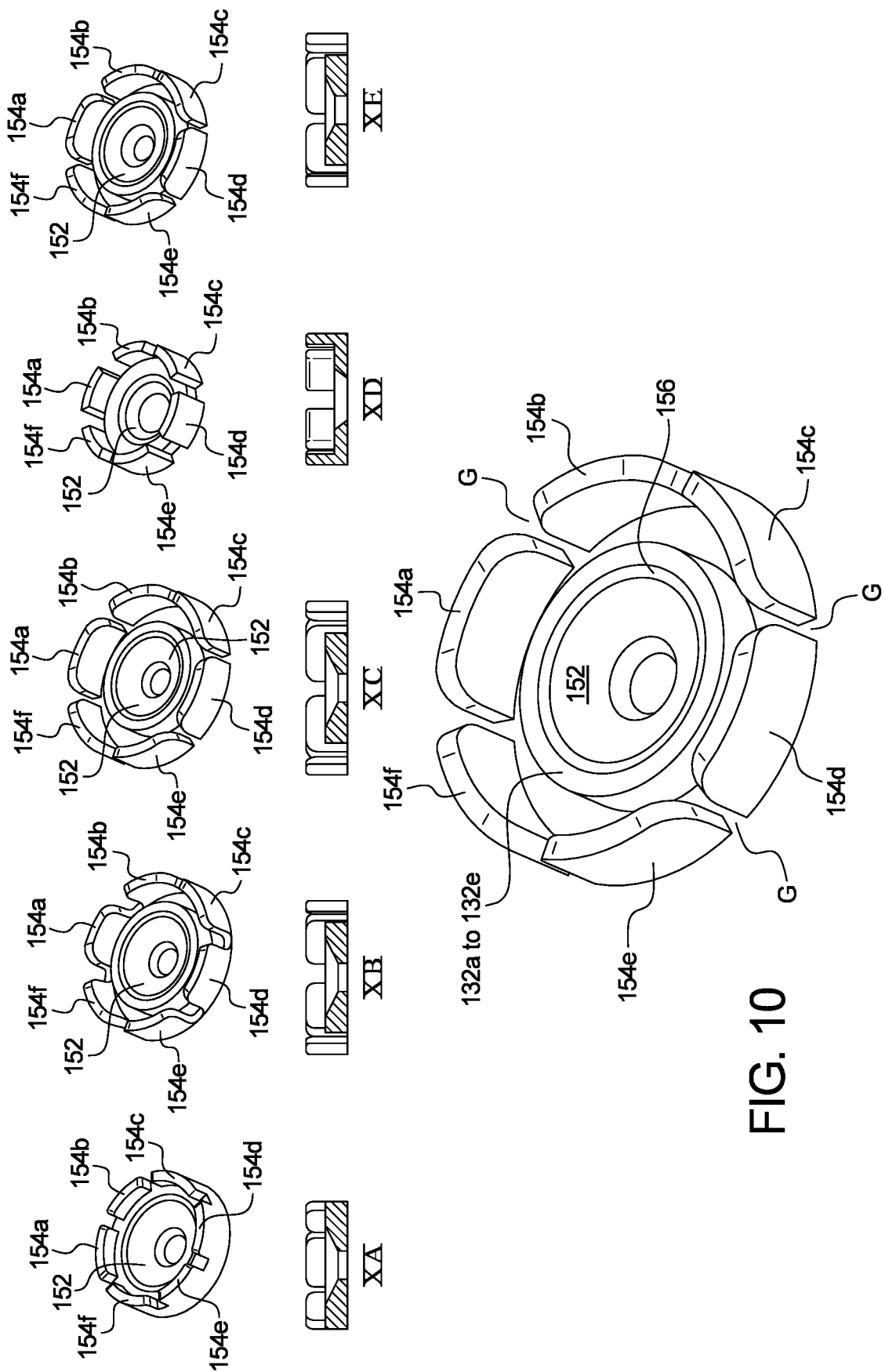
FIG. 10 includes perspective and elevation sectioned views illustrating multiple alternative embodiments for the valve seats of the present disclosure.

FIGS. 7 and 10 illustrate that any of valve seats 132a to 132e described herein may include a tapered sealing surface 152 surrounded by a plurality of displacement ribs 154a to 154f, wherein the displacement ribs may extend from rigid body 138 of disposable cassette 130, and wherein at least some of displacement ribs 154a to 154f are spaced apart by gaps G to prevent or mitigate against an unwanted occlusion of tapered sealing surface 152 by flexible sheet 136 and to allow fresh or used dialysis fluid to flow therethrough. Displacement ribs 154a to 154f may be completely separate from each other (see examples XC to XE in FIG. 10) or extend from a common cylindrical base (see examples XA and XB in FIG. 10). Displacement ribs 154a to 154f may also be separate from the tapered sealing surface 152 (see examples XB, XC and XE in FIG. 10) or extend from or be connected to an outer edge of the tapered sealing surface (see examples XA and XD in FIG. 10). Displacement ribs 154a to 154f help to guide pinch valve plunger 84 towards a center of the valve seat 132a to 132e, while also providing an amount of give or play between the pinch valve plunger and the valve seat. Tapered sealing surface 152 in an embodiment tapers to form a funnel shape leading to an opening that allows fresh or used dialysis fluid to flow into or out of valve seat 132a to 132e. In an embodiment, opening extends through a port 140a to 140e located on the other side of rigid body 138 of disposable cassette 130 (FIG. 8). Tapered sealing surface 152 may also include or define one or more circular sealing ring 156 that presses into flexible sheet 136 when the flexible sheet is closed by a pinch valve 34a to 34e.

In an embodiment, a first or patient pressure sensing pod 150a is located in disposable cassette 130 directly adjacent to patient line valve seat 132e. Patient pressure sensing pod 150a when disposable cassette 130 is loaded against a first or patient pressure sensor 36a, which outputs to cycler control unit 50. The output of patient pressure sensor 36a may be used to control positive and negative pumping pressures experienced by the patient so as to be within safe pressure limits, e.g., within 0.21 bar (3 psig) positive pressure and −0.10 bar (−1.5 psig) negative pressure. A second or pumping pressure sensing pod 150b is located in disposable cassette 130 between common well 146 and the second peristaltic tube port 142b. Pumping pressure sensing pod 150b when disposable cassette 130 is loaded is abutted against a second or pumping pressure sensor 36b, which outputs to cycler control unit 50. The output of pumping pressure sensor 36b may be used to detect supply and drain line occlusions and/or supply and drain container empty conditions. For example, a jump in positive pressure from pumping pressure sensor 36b may indicate an occlusion in drain line 122a or patient line 122e. In another example, a jump in negative pressure from pumping pressure sensor 36b may indicate (i) an occlusion in patient line 122e or supply lines 122b to 122d, (ii) a supply container 124b, 124c or last fill container 124d empty condition during treatment, or (iii) a supply container 124b, 124c, last fill container 124d or drain container 124a empty condition at the end of treatment while attempting to pump any residual fresh or used treatment fluid to drain.

Disposable cassette 130 may also include one or more area 148, which when mounted for operation abuts against a thermocouple or other type of temperature sensor 38 outputting to control unit 50. Temperature sensing area 148 may for example be placed at the end of inline fluid heating pathway 144 directly adjacent to patient pressure sensing pod 150a, so that the outlet temperature of the fresh dialysis fluid to the patient may be monitored and controlled to a desired temperature, e.g., body temperature or 37° C. and e.g., via a proportional, integral, derivative ("PID") routine performed by control unit 50 using feedback from temperature sensor 38. A second temperature sensor and associated cassette temperature area (not illustrated) may be located so as to detect a temperature at the inlet of inline fluid heating pathway 144 if needed, which may likewise provide useful information for the PID routine.

FIG. 6 illustrates disposable cassette 130 disposed vertically as it is loaded for operation against actuation surface 30, wherein the cassette includes multiple features that enhance priming and air handling. Viewing FIG. 1 additionally, it should be appreciated that an important feature of overall system 10 for preventing air from reaching the patient is the location of fresh dialysis fluid supply containers or bags 124b and 124c and last fill container or bag 124d elevationally above where disposable cassette 130 is loaded against the actuation surface, behind door 24. Here, air tends to remain in containers or bags 124b to 124d and not be delivered to disposable cassette 130. Although not illustrated, it is contemplated to provide structure within and on top of bag shelf enclosure 40 that raises a back end of each container or bag 124b to 124d relative to a front, discharge end of the containers. In this manner, air tends to migrate towards the back of containers 124b to 124d, away from the connection of the bags to respective tubing 122b to 122d.

It is also contemplated to place air sensors or detectors (not illustrated), which may be ultrasonic sensors having emitter and receiver pairs on either side of holes or slots 26b to 26d as illustrated in FIG. 1. The air sensors or detectors output to control unit 50, which monitors their output signals. If air is detected, control unit 50 (i) stops peristaltic pump actuator 60 from pumping any further towards the patient (ii) closes the corresponding supply valve seat 132b to 132d illustrated in FIG. 6, (iii) opens drain valve seat 132a, and (iv) reverses peristaltic pump actuator 60 to force the dialysis fluid having entrained air into drain line 122a and drain container 124a.

FIG. 6 illustrates that drain valve seat 132a is located elevationally above supply valve seat 132b to 132d to aid the air in migrating towards the drain valve seat. Additionally, the top of common well 146 is provided with a ramp 146r for guiding the air up towards drain valve seat 132a. FIG. 6 further illustrates that pumping pressure sensing pod 150b is provided with an inlet that is lower than the top of ramp 146r, such that air is encouraged to buoy away from pumping pressure sensing pod 150b up towards drain valve seat 132a. FIG. 6 further illustrates that the outlets of patient and pumping pressure sensing pods 150a and 150b are directed upwardly and to a relatively elevationally high location, such that air tends to leave the pods to aid in the accuracy of fresh and used dialysis fluid pressure measurements.

To aid priming, serpentine fluid heating pathway 144 winds upwardly to help air leave disposable cassette 130 during priming through patient line valve seat 132e and patient line 122e to atmosphere. Patient line valve seat 132e, like drain line valve seat 132a, is located relatively elevationally high when disposable cassette 130 is loaded for operation. During priming, the distal end of patient line 122e is held in a priming holder (not illustrated) located on the housing 22 of cycler 20. An additional air detector or sensor (not illustrated) outputting to control unit 50, e.g., an ultrasonic sensor, may be incorporated into the priming holder to detect when patient line 122e is fully primed with fresh dialysis fluid. It is also contemplated to place an additional air sensor or detector (not illustrated) for the patient line, which may again be an ultrasonic sensor having an emitter and receiver pair located on either side of patient line hole or slot 26e illustrated in FIG. 1. The additional air sensor or detector outputs to control unit 50, which monitors its output signals. If air is detected in patient line 122e, control unit 50 runs the air purge procedure (i) to (iv) just described, pushing the air back through fluid heating pathway 144 to drain container or bag 124a.

Pressure Sensor

Figure 11:
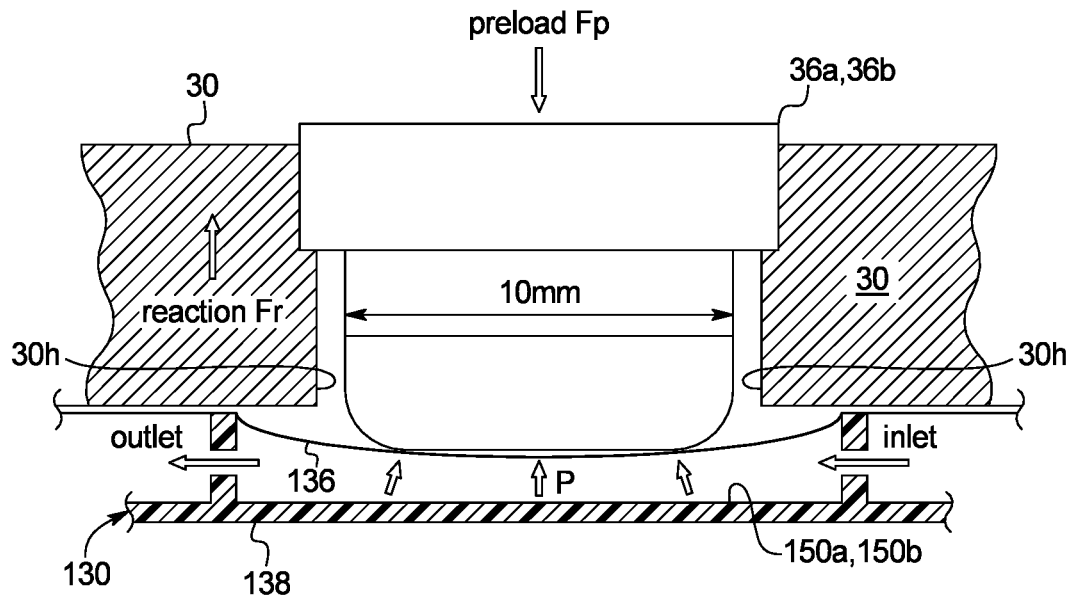
FIG. 11 is a sectioned elevation view illustrating one embodiment for interfacing the pressure sensors and pressure sensor pods of the present disclosure.

Referring now to FIG. 11, cycler 20 of system 10 in one embodiment mounts pressure sensors 36a, 36 to, or in relation to, actuation surface 30 of the cycler so as to reside within a hole 30h in actuation surface 30, and such that when disposable cassette 130 is loaded for operation, cassette sheeting 136, which may be polyvinyl chloride ("PVC") or any of the other polymers listed herein, is contacted and placed under tension by the pressure sensor 36a, 36b, creating a baseline or preload force Fp measured by the pressure sensor. FIG. 11 illustrates one possible diameter for the contacting head of pressure sensor 36a, 36b, namely, 10 mm, which also provides an indication for the size or diameter of pressure pods 150a, 150b of disposable cassette 130. Fresh or used dialysis fluid pressure P displaces (or attempts to displace) cassette sheeting 136 further and thereby increases or decreases a reaction fluid force Fr acting on pressure sensor 36a, 36b relative to baseline or preload force Fp. The force differences between Fr and Fp caused by positive or negative fluid pressure P are correlated to actual fluid pressure values by control unit 50, which are used for pressure control as described herein, and which may be displayed by user interface 58 and/or stored for delivery to a remote server computer for evaluation.

The pre-tensioning of cassette sheeting 136 by pressure sensor 36a, 36b results in a pressure sensing regime having high sensitivity and resolution, but which may be prone to temperature sensitivity. It is accordingly contemplated to program control unit 50 to compensate pressure readings for temperature. Here, a voltage output (could alternatively be a current output) from pressure sensor 36a, 36b is modified by adding an offset component, which is a function of a measured temperature (e.g., using temperature sensor 38 and temperature sensing area 148 discussed above) multiplied by an empirically determined temperature scaling coefficient, to form a compensated voltage output, which is then converted or correlated to a compensated positive or negative pressure. One suitable scaling or offset algorithm stored in control unit 50 is as follows:

$$V_T = V_0 + gT, \text{ wherein}$$

$V_0$ is the output from pressure sensor 36a, 36b,
$V_T$ is a modified pressure output used going forward by control unit 50,
g is a temperature scaling coefficient, and
T is the sensed temperature.

Figure 12:
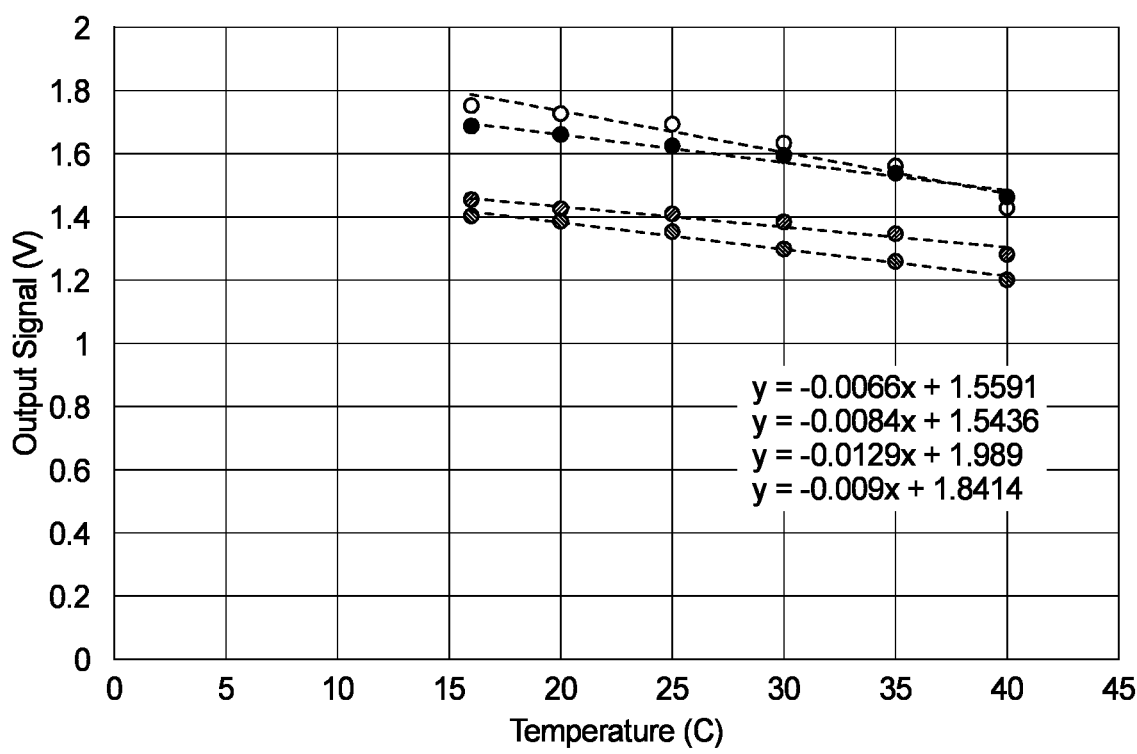
FIG. 12 is a plot illustrating pressure sensor output versus temperature, which is used to determine a temperature scaling coefficient for a pressure sensing scaling or offset equation of the present disclosure.

FIG. 12 illustrates a plot used to determine the temperature scaling coefficient g for the above scaling or offset algorithm. For each of the four plot lines, the baseline or preload force Fp of pressure sensor 36a, 36b was observed during a fluid dwell period of thirty minutes for fluids maintained at different temperatures ranging from 15° C. to 40° C. (typical dialysis fluid temperatures). An equation characterizing each line was determined as illustrated in FIG. 12. Each equation takes the form of y=mx+b, where (i) y is $V_T$ above, (ii) b is $V_0$ above, (iii) x is the measured temperature T above, and (iv) m is the scaling coefficient g above. The m values from each trial were averaged to form the scaling coefficient g used in the scaling or offset algorithm stored in control unit 50.

In an embodiment, control unit 50 is configured to update the compensation algorithm for an adjustment in measured temperature T (i) each time the output from the pressure sensor is read by the control unit or (ii) on a periodic basis. Control unit 50 is configured to use the modified output $V_T$ from pressure sensors 36a, 36b for at least one of (a) controlling the medical fluid pump actuator to pump within a positive or negative patient pressure limit, (b) determining a line occlusion condition, and/or (c) determining a fresh or used dialysis fluid container empty condition during or after treatment.

As mentioned above, the pre-tensioning of cassette sheeting 136 via pressure sensors 36a, 36b results in a pressure sensing regime having high sensitivity and resolution, but which may also be prone to mechanical creep sensitivity. To combat creep sensitivity, control unit 50 is programmed in one embodiment to precondition cassette sheeting 136 prior to treatment, e.g., during setup, so that much of the variance to the pressure signal due to creep is eliminated before the measurements from pressure sensors 36a, 36b matter. To do so, control unit 50 after disposable cassette 130 is primed for treatment causes all pinch valves 34a to 34e to close and then actuates peristaltic pump actuator 60 so as to pressurize the inside of cassette 130, including the sheeting at pressure pods 150a, 150b, to stretch the cassette sheeting. Control unit 50 may be programmed to cause pump actuator 60 to oscillate the cassette fluid pressure up and down cyclically multiple times, and perhaps in different directions, over a specified duration. An upper pressure may be, for example, from 100% to 150% of a maximum operational pressure set for treatment, wherein the maximum operational pressure may be higher than the patient pressure limits. For example, pressures used for priming or during the drain purge discussed above may be higher, e.g., 0.50 bars (7.25 psig) or higher. The preconditioning of cassette sheeting 136 helps to make the uncompensated pressure reading more accurate, while the temperature compensation helps to make the final pressure reading more accurate.

Load Cell Calibration

Figure 13:
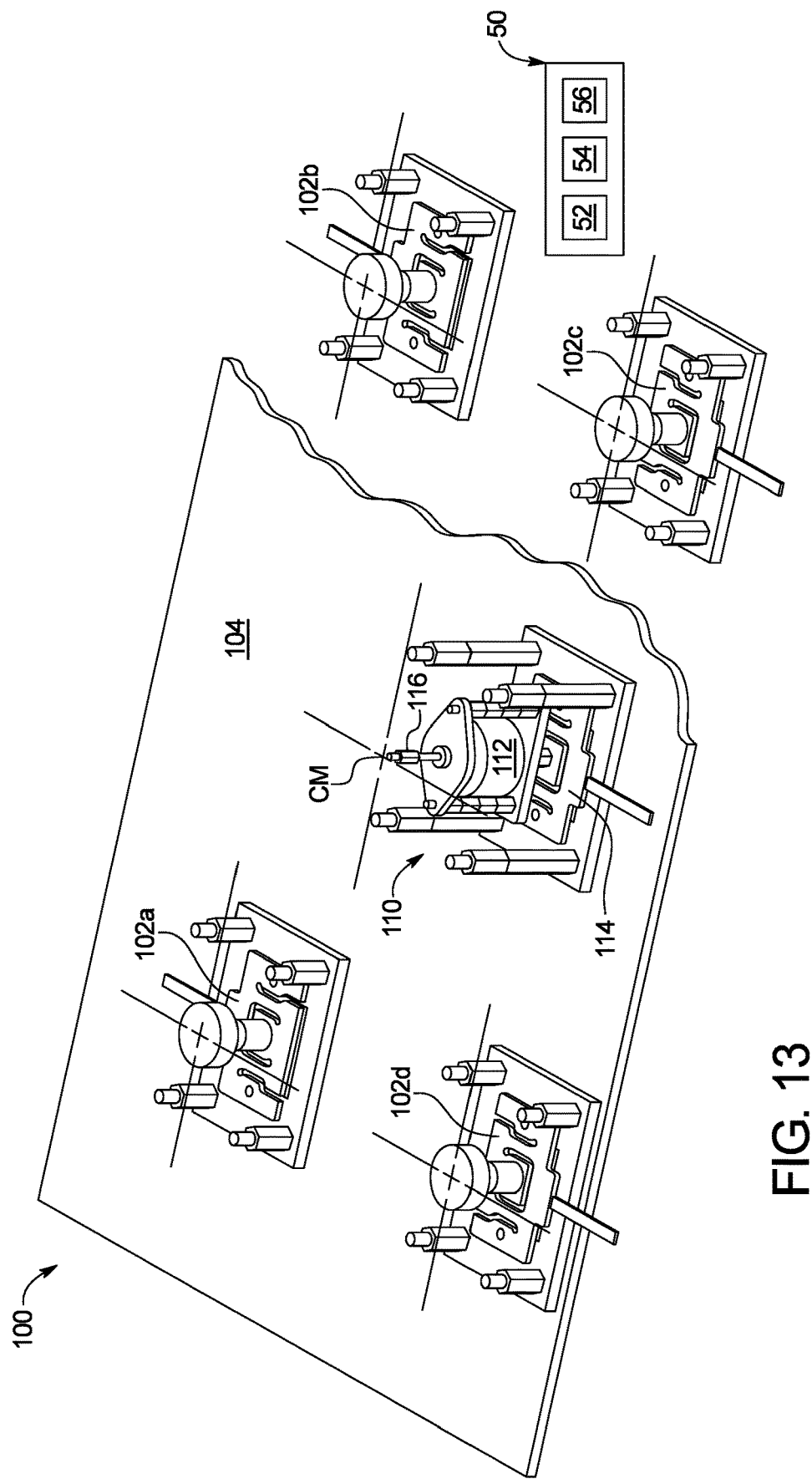
FIG. 13 is a perspective view of one embodiment for a self-calibrating weigh scale useable with the system and cycler of the present disclosure.

Referring now to FIG. 13, system 10 and cycler 20 of the present disclosure in one embodiment employ a weigh scale 100 including multiple operational load cells 102a to 102d to monitor the amount of fresh dialysis fluid delivered to the patient, the amount of used dialysis fluid removed from the patient, and from there enable control unit 50 to calculate an amount of ultrafiltration ("UF") removed from the patient. Weigh scales and load cells are advantageous for a number of reasons. First, weigh scale 100 is relatively accurate compared with other volumetric measurement techniques. Second, weigh scale 100 reduces the pump cost because pump actuator 60 may be a relatively simple peristaltic pump actuator and the disposable portion of the pump may be a simple peristaltic pump tube 126.

One drawback of the use of load cells is calibration. Load cells may over time read inaccurately and therefore need to be recalibrated. Present cycler 20 and associated system 10 provide a weigh scale 100 having multiple load cells 102a to 102d and an onboard structure 110 and associated methodology for calibrating weigh scale 100. In one embodiment, weigh scale 100 includes a weigh plate 104 located at the top of cycler 20, which supports the weight of bag shelf enclosure 40 and each of the solution and drain containers 124a to 124d and associated fresh and used dialysis fluid. Weigh plate 104 and each of the weighted items on the weigh plate are supported by multiple, e.g., four, load cells 102a to 102d that collectively measure the total mass placed on the weigh plate (bag shelf enclosure 40, containers 124a to 124d and fluids). Onboard calibration structure 110 in one embodiment includes a linear actuator 112 (may be of the same type as used for the pinch valves, e.g., include a motor and lead screw or a linear stepper motor) and a fifth or calibration load cell 114 located beneath linear actuator 112, wherein linear actuator 112 includes an actuation output shaft 116, which is fixed to weigh plate 104. Actuation output shaft 116 may for example extend through a hole formed in weigh plate 104 and be capped above the upper surface of the weigh plate so as to be able to provide a downward force onto the plate. Actuation output shaft 116 may alternatively include a flange that is bolted to the underside of weigh plate 104 or that slides into a groove formed on the underside of weigh plate 104, be threaded to thread into the underside of weigh plate 104, or have some alternative mechanical connection to weigh plate 104.

Linear actuator 112 in one embodiment is actuated so as to apply a pulling or downward force to of weigh plate 104. In one implementation, the force is applied to the center of mass CM of weigh plate 104 as illustrated in FIG. 13. Operational load cells 102a to 102d in an embodiment are each at least substantially equidistant from the center of mass CM and are spread out from each other in equal x-coordinate distances (e.g., the distance between the contact points of load cells 102a and 102b being the same as the distance between the contact points of load cells 102*d* and 102*c*), and in equal y-coordinate distances (e.g., the distance between the contact points of load cells 102*a* and 102*d* being the same as the distance between the contact points of load cells 102*b* and 102*c*).

Additional calibration load cell 114 measures the total pulling or downward force applied by linear actuator 112, while the four operational load cells 102*a* to 102*d* each measure a fraction or fourth of the total force. If operational load cells 102*a* to 102*d* are each performing properly, the sum of their outputs should equal the total force measured by calibration load cell 114. In an example, suppose 1000 Newtons ("N") of pulling force is applied by linear actuator 112. Calibration load cell 114 should output 1000 N, while operational load cells 102*a* to 102*d* should each read 250 Newtons, totaling in combination 1000 N.

Because calibration load cell 114 is used infrequently, the calibration algorithm is applied assuming that the output of calibration load cell 114 is more accurate than the collective output of the operational load cells 102*a* to 102*d*, which are used throughout each treatment. So if during calibration there is a mismatch between what the calibration load cell 114 reads versus the collective output of the operational load cells 102*a* to 102*d*, control unit 50 using the calibration algorithm scales or offsets the collective output of the operational load cells 102*a* to 102*d* to match that of the calibration load cell 114. In the above example, suppose operational load cells 102*a* to 102*d* actually collectively read 995 N instead of 1000 N. Operational load cells 102*a* to 102*d* are accordingly reading low by 0.5%. Control unit 50 of cycler 20 is thereby configured during treatment to modify the collective output of the operational load cells 102*a* to 102*d* by a calibration factor of 1000/995 or 1.005.

The load cell calibration routine or algorithm of system 10 is performed on some desired basis, e.g., before the start of each treatment. Control unit 50, for example, controls a duration of an operation (patient fill or drain) of pump actuator 60 using offsetted output pressures from operational load cells 102*a* to 102*d*. Control unit 50 is configured to cause linear actuator 112 to not supply any force during such duration of operation. Control unit 50 in another example is configured to use two or more offsetted outputs from operational load cells 102*a* to 102*d* to determine a mass or volumetric flowrate during treatment. In a further example, control unit 50 is configured to determine an amount of fresh dialysis fluid delivered using at least two offsetted outputs from the operational load cells 102*a* to 102*d*. In yet another example, control unit 50 is configured to determine an amount of used dialysis fluid delivered using at least two offsetted outputs from the operational load cells 102*a* to 102*d*. In yet a further example, control unit 50 is configured to determine an amount of fresh dialysis fluid delivered to or used dialysis fluid removed from a patient using at least two offsetted outputs from the operational load cells 102*a* to 102*d*.

It should also be appreciated that because many of the weight values monitored and collected during treatment are weight differences, error in the collective output of operational load cells 102*a* to 102*d* tends to cancel itself out, assuming that the error does not change over the course of treatment. For example, the mass associated with a patient fill volume of, e.g., two liters is monitored and controlled by the collective output of the operational load cells 102*a* to 102*d* by recording a drop in mass over the course of the patient fill. The volume and mass associated with a patient drain may be preset in control unit 50, e.g., be a factor, such as 1.3, multiplied by the fill volume to account for patient UF removed into the drain volume. The volume and mass associated with a patient drain may alternatively be left open-ended and be controlled instead by the sensing of a characteristic rise in negative pressure by pumping pressure sensing pod 150*b* and associated pressure sensor 36*b*, indicating that the patient is essentially fully drained and that further draining may be uncomfortable for the patient. In either case, operational load cells 102*a* to 102*d* sense an increase in weight over the course of the patient drain, which should tend to cancel any error in the operational load cells.

It should be understood that various changes and modifications to the presently preferred embodiments described herein will be apparent to those skilled in the art. It is therefore intended that such changes and modifications be covered by the appended claims. For example, while system 10 discloses peristaltic pumping, membrane or volumetric pumping may be used instead. Also, while system 10 discloses inline heating, batch heating may be used instead. Further, while the calibrated load sensing is disclosed in connection with supply containers and drain containers, the calibrated load sensing may be used instead with a dialysis fluid preparation unit that pumps to one or more weigh container placed on the weigh plate.

The invention is claimed as follows:

1. A peritoneal dialysis system comprising:
a cycler including a pump actuator;
a disposable set including
  a pumping portion operable with the pump actuator,
  a patient line positioned to fluidly communicate with the pumping portion, and
  a drain container positioned to fluidly communicate with the pumping portion; and
a control unit configured to cause the pump actuator to actuate the pumping portion (i) to run a peritoneal dialysis treatment in which fresh dialysis fluid is pumped through the patient line to a patient and used dialysis fluid is pumped from the patient to the drain container, and (ii) at the end of treatment, to pump the used dialysis fluid from the drain container, through the patient line, to a house drain.

2. The peritoneal dialysis system of claim 1, wherein the pump actuator is a peristaltic pump actuator and the pumping portion of the disposable set includes a peristaltic pump tube.

3. The peritoneal dialysis system of claim 1, which includes an extension line configured to be connected to the patient line if needed to reach the house drain.

4. The peritoneal dialysis system of claim 3, wherein the extension line is reusable.

5. The peritoneal dialysis system of claim 1, which includes a user interface communicating with the control unit, and wherein the user interface is configured to prompt a patient at the end of treatment to disconnect from the patient line and to move the patient line towards the house drain.

6. The peritoneal dialysis system of claim 1, which includes a user interface communicating with the control unit, and wherein the user interface is configured to provide or enable a drain button at the end of treatment for initiating the pumping of the used dialysis fluid from the drain container, through the patient line, to the house drain.

7. The peritoneal dialysis system of claim 6, wherein the user interface is further configured to require a confirmation that the drain line is in fluid communication with the house drain prior to providing or enabling the drain button.

8. The peritoneal dialysis system of claim 1, wherein the cycler includes a patient valve actuator that operates with a patient valve seat provided by the disposable set, and a drain valve actuator that operates with a drain valve seat provided by the disposable set, and wherein the control unit is configured to cause the patient valve actuator and the drain valve actuator to allow flow through the patient valve seat and the drain valve seat to pump the used dialysis fluid from the drain container, through the patient line, to the house drain.

9. The peritoneal dialysis system of claim 8, wherein at least one of the patient valve actuator or the drain valve actuator is a pinch valve actuator.

10. The peritoneal dialysis system of claim 1, which includes a supply container positioned to fluidly communicate with the pumping portion of the disposable set, wherein the supply container is used during the peritoneal dialysis treatment for pumping fresh dialysis fluid through the patient line to the patient.

11. The peritoneal dialysis system of claim 10, wherein the supply container is used later during the peritoneal dialysis treatment for receiving used dialysis fluid from the patient.

12. The peritoneal dialysis system of claim 11, wherein the cycler includes a sensor in operable communication with the control unit, and wherein the control unit is configured to use an output from the sensor to determine when one of the drain container or the supply container used later as a drain container is empty or substantially empty after pumping its used dialysis to the house drain, and to thereafter switch to the other of the drain container or the supply container used later as a drain container to pump its used dialysis to the house drain.

13. The peritoneal dialysis system of claim 12, wherein the sensor is a weight sensor or a pressure sensor.

14. The peritoneal dialysis system of claim 10, wherein the control unit is further configured to cause the pump actuator to actuate the pumping portion at the end of treatment to pump remaining fresh dialysis fluid from the supply container, through the patient line, to the house drain.

15. The peritoneal dialysis system of claim 1, wherein the drain container is a first drain container and which includes a second drain container positioned to fluidly communicate with the pumping portion of the disposable set, wherein the cycler includes a sensor in operable communication with the control unit, and wherein the control unit is configured to use an output from the sensor to determine when the first drain container is empty or substantially empty after pumping its used dialysis to the house drain, and to thereafter switch to the second drain container to pump its used dialysis to the house drain.

16. The peritoneal dialysis system of claim 15, wherein the sensor is a weight sensor or a pressure sensor.

17. The peritoneal dialysis system of claim 1, wherein the drain container is a first drain container, and which includes a second drain container positioned to fluidly communicate with the pumping portion of the disposable set, and wherein the control unit is configured to drain the first and second drain containers at the same time.

18. A peritoneal dialysis system comprising:
a cycler including a pump actuator;
a disposable set including
a pumping portion operable with the pump actuator,
a patient line positioned to fluidly communicate with the pumping portion, and
a drain line positioned to fluidly communicate with the pumping portion; and
a control unit configured to cause the pump actuator to actuate the pumping portion (i) to run a peritoneal dialysis treatment in which fresh dialysis fluid is pumped through the patient line to a patient and used dialysis fluid is pumped from the patient though the drain line, and (ii) at the end of treatment, to pump the used dialysis fluid through the drain line and the patient line, to a house drain.

19. The peritoneal dialysis system of claim 18, wherein the drain line is in fluid communication with a drain container, and wherein the drain container is provided initially as a drain container or a supply container filled with fresh dialysis fluid.

20. The peritoneal dialysis system of claim 18, wherein the patient line and the drain line are separated by a disposable cassette of the disposable set, and wherein at the end of treatment, the used dialysis fluid is pumped through the drain line, through the disposable cassette, and through the patient line, to the house drain.

21. The peritoneal dialysis system of claim 20, wherein the disposable cassette includes a pressure sensing pod positioned to enable a pressure change indicative of a drain container in fluid communication with the drain line being empty to be detected, and wherein the control unit thereafter causes a switch to draining used dialysis fluid from a different source at the end of treatment to the house drain.

22. The peritoneal dialysis system of claim 18, wherein the cycler includes a weigh scale, wherein a drain container in fluid communication with the drain line is located so as to be weighed by the weigh scale, and wherein an output from the weigh scale indicative of the drain container being empty is used by the control unit to cause a switch to draining used dialysis fluid from a different source at the end of treatment to the house drain.

23. A peritoneal dialysis system comprising:
a cycler including a pump actuator;
a disposable set including
a pumping portion operable with the pump actuator,
a patient line positioned to fluidly communicate with the pumping portion, and
a drain container positioned to fluidly communicate with the pumping portion; and
a control unit configured to cause the pump actuator to actuate the pumping portion (i) to run a peritoneal dialysis treatment in which fresh dialysis fluid is pumped through the patient line to a patient and used dialysis fluid is pumped from the patient to the drain container, and (ii) at the end of treatment, to pump the used dialysis fluid from the drain container, through the patient line, to a desired destination.

24. The peritoneal dialysis system of claim 23, wherein the desired destination includes a house drain or another container positioned to fluidly communicate with the pumping portion.

25. The peritoneal dialysis system of claim 23, wherein pumping the used dialysis fluid from the drain container through the patient line during (ii) includes actuating the pumping portion in a first direction to at least partially fill the patient line with the used dialysis fluid and then actuating the pumping portion in a second direction to remove the used dialysis from the patient line to the desired destination.

* * * * *